US005789210A

United States Patent [19]
Ho et al.

[11] Patent Number: 5,789,210
[45] Date of Patent: Aug. 4, 1998

[54] RECOMBINANT YEASTS FOR EFFECTIVE FERMENTATION OF GLUCOSE AND XYLOSE

[75] Inventors: Nancy W. Y. Ho; George T. Tsao, both of West Lafayette, Ind.

[73] Assignee: Purdue Research Foundation, West Lafayette, Ind.

[21] Appl. No.: 148,581

[22] Filed: Nov. 8, 1993

[51] Int. Cl.$^6$ .................. C12P 7/08; C12N 1/19; C12N 15/81; C07H 21/04

[52] U.S. Cl. .................. 435/163; 435/172.3; 435/254.2; 435/254.21; 435/320.1; 536/23.2; 536/23.7; 536/23.74

[58] Field of Search .................. 435/172.3, 183, 435/194, 254.21, 320.1, 163, 69.1, 172.1, 254.1, 254.11, 254.2, 161, 162, 165; 536/23.1, 23.2, 23.7, 23.74

[56] References Cited

PUBLICATIONS

Ammerer, G., "Expression of genes in yeast using the ADC1 promoter," Methods in Enzymol. 101, 192–201 (1983).

Becker, D., and L. Guarente, "High efficiency transformation of yeast by electroporation," Methods in Enzymol. 194, 182–186 (1991).

Bennetzen, J. L. and B. D. Hall, "The primary structure of the Saccharomyces cerevisiae gene for alcohol dehydrogenase I," J. Biol. Chem., 257(6), 3018–3025 (1982).

Chang, S.F. and N.W.Y. Ho, "Cloning the yeast xylulokinase gene for the improvement of xylose fermentation." Appl. Biochem Biotechnol. 17, 313–318 (1988).

Chen, Zhengdao, and N.W.Y. Ho, "Cloning and improving the expression of Pichia stipitis xylose reductase gene in Saccharomyces cerevisiae," Appl. Biochem. Biotechnol., 39–40, 135–147 (1993).

Chevallier, M. R. and M. Aigle, "Qualitative detection of penicillinase produced by yeast strains carrying chimeric yeast–coli plasmids," FEBS Letters, 108(1) 179–184 (1979).

Chiang, L–C, H–Y. Hsiao, P. P. Ueng, L–F. Chem, and G. T. Tsao. "Enthanol production from xylose by enzymic isomerization and yeast fermentation," Biotechnol. Bioeng., 11, 263–274 (1981).

D'Amore, C. G., I. Russell, and G. G. Stewart, "Selection and optimization of yeast suitable for ethanol production at 40°C." Enz. Microbiol. Technol., 11, 411 (1989).

D'Amore, T., C. J. Panchal, I. Russell, and G.G. Stewart, "A study of ethanol tolerance in yeast: Critical Reviews," Biotechnol., 9, 287 (1990).

Deng, X. X. and N.W.Y. Ho, "Xylulokinase activity in various yeasts including Saccharomyces cerevisiae containing the cloned xylulokinase gene," Appl. Biochem. Biotechnol., 24–25, 193 (1990).

Grootjen, D.R.J., R.G.J.M. van der lans, and K. Ch.A.M. Luyben, Effects of the aeration rate on the fermentation of glucose and xylose by Pichia stipitis CBS 5773, Enzyme Microb. Technol., 12, 20–23 (1990).

Hallborn, J., M. Walfridsson, U. Airaksinen, H. Ojamo, B. Hahn–Hagerdal, M. Penttila, and S. Keranen, Xylitol production by recombinant Saccharomyces cerevisiae, Bio./Technol., 9, 1090 (1991).

Ho, N.W.Y., P. Stevis, S. Rosenfeld, J. J. Huang, and G. T. Tsao, "Expression of E. coli xylose isomerase gene by a yeast promoter," Biotechnology and Bioenginering Symposium, No. 13, 245–250 (1983).

Holland, J. P. and M. J. Holland, "The primary structure of a glyceraldehyde–3–phosphate dehydrogenase gene from Saccharomyces cerevisiae," J. Biol. Chem. 253(19) 9839–9845 (1979).

Jeffries, T. W., Emerging technology for fermenting D–xylose: Trends in biotechnology 3(8), 208–212 (1985).

Jeffries, T. W., "Utilization of xylose by bacteria, yeasts, and fungi," Adv. in Biochem. Engr. Biotechnol. 27, 1–32 (1983).

Kötter, P. and M. Ciriacy, "Xylose fermentation by Saccharomyces cerevisiae," Appl. Microbiol. Biotechnol., 38, 776–783 (1993).

Kunkel, T. A., J. P. Roberts, and R. a. Zakour, "Rapid and efficient site-specific mutagenesis without phenotypic selection," Methods Enzymol., 154, 367–382 (1987).

Lastick, S.,M. Y. Tucker, J. R. Beyett, G. R. Noll, and K. Grohmann, "Stimultaneous fermentation and isomerization of xylose to ethanol," Appl. Microbiol. Biotechnol., 30, 574–579 (1989).

Rosenfeld, S., P. Stevis, and N.W.Y. Ho, "Cloning and characterization of the xyl genes from E. coli," Mol. Gen. Genetics, 194, 410–415 (1984).

Sarthy, A. V., et al., Expression of the E. coli xylose isomerase gene in S. cerevisiae, Appl. Environ. Microb., 53, 1996–2000 (1987).

Stevis, P. A., J. J. Huang, N.W.Y. Ho, "Cloning of the pachysolen tannophilus xylulokinase gene by complementation in Escherichia coli," Appl Environ. Micro. (53) 1, 2975–2977 (1987).

Stevis, P. A. and N.W.Y. Ho, "Overproduction of D–xylose isomerase in E. coli by Cloning the D–xylose Isomerase gene", Enzyme Microb. Technol., vol. 7, pp. 592–596 (1985).

Strasser, A.W.M., C. P. Hollenberg, M. Ciriacy, P. Köetter, R. Amore, M. Piontel, and J. Hagedorn, "Cloning of yeast xylose reductase and xylitol dehydrogenase genes and their use," German patent application (1990).

(List continued on next page.)

Primary Examiner—David Guzo
Attorney, Agent, or Firm—Woodard, Emhardt, Naughton Moriarty & McNett

[57] ABSTRACT

Described are recombinant yeasts containing genes encoding xylose reductase, xylitol dehydrogenase and xylulokinase, and DNA molecules, vectors and methods useful for producing such yeasts. The recombinant yeasts effectively ferment xylose to ethanol, and preferred yeasts are capable of simultaneously fermenting glucose and xylose to ethanol thereby taking full advantage of these two sugar sources as they are found in agricultural biomass.

20 Claims, 18 Drawing Sheets

PUBLICATIONS

Takuma, S., N. Nakashima, M. Tantirungkij, S. Kinoshita, H. Okada, T. Seki, and T. Yoshida, "Isolation of xylose reductase gene of *Pichia stipitis* and its expression in *Saccharomyces cerevisiae*," Appl. Biochem. Biotechnol., 27–28, 327 (1991).

Toivola, A., D. Yarrow, E. van den Bosch, J. P. van Dijken, and W. A. Scheffers, "Alcoholic fermentation of D-xylose by yeasts," Appl. Environ. Microbiol., 47(6), 1221–1223 (1984).

Wilhelm, M., and C. P. Hollenberg, "Selective cloning of *Bacillus subtilis* xylose isomerase and xylulokinase in *E. coli* genes by IS5–mediated expression," the EMBO Journal, 3, 2555–2560 (1984).

Zalkin, H. and C. Yanofsky, J. Biol. Chem. 257, 1491–1500 (1982).

Amore et al. (1989). Appl. Microbiol. Biotechnol. 30, 351–357.

Burke et al. (1983). J. Biolog. Chem. 258(4).2193–2201.

Ho et al. (1989). Enzyme Microb. Technol. 11, 417–421.

Kötter et al. (1990). Curr. Genet. 18, 493–500.

The xylose metabolic pathways in microorganisms.

——— Xylose non-utilizing yeasts (*Saccharomyces cerevisiae, Schizosaccharomyces pombe*, etc.)

——— Xylose utilizing yeasts (*Candida shehatae, Pichia stipitis, Pachysolen tannophilus*, etc.)

------- Bacteria (*E. coli, Bacillus* species, *Streptomyces* species, etc.)

Fig. 2a

```
1321  CTGGTCACCGATAAGTATCACCCCTCTCCGAACTATCATCTTTCATTCATCCAACTCTCCAAACCATTATATGGTATGATTTGTTATTGTAATGGTATGATGTTCTTTGGCAAGGGAGAGGATA
      L  V  T  D  K  Y  H  P  S  P  N  Y  H  L  F  I  H  P  T  L  P  N  H  Y  M  G  M  I  C  Y  C  N  G  S  L  A  R  E  R  I

1441  ACAGACCAGTTAAACAACAAAGAACGGCAAAATAATTATGACAAGCTGCTCTAGATTGCACACTCTTTTTAATCAAGCTCTGCCTACAGATCACTCAGAAACTACTGAAAATGAATTAGGTGTATATTTT
      R  D  E  L  N  K  E  R  E  N  N  Y  E  K  T  N  D  W  T  L  F  N  Q  A  V  L  D  D  S  E  S  S  E  N  E  L  G  V  Y  F

1561  CCCTCTGGGGAGATCGTTCCTAGCGTAAAAGCCATAAACAAAAGGGTTATCTTCAATCAAAAACGGGTCTATGATTGAAAGACAGGTCGCCAAGTTCAAAGACAAGAGGCCACCATCCCAAA
      P  L  G  E  I  V  P  S  V  K  A  I  N  K  R  V  I  F  N  P  K  T  G  M  I  E  R  E  V  A  K  F  K  D  K  R  H  D  A  K

1681  AATATTGTAGAATCACAGGCTTTAAGTTGCAGGGTAAGAATATCTCCCCTGCTTCCGGATTCAAACGCAAGCTCACAACACACTCAACGAAGATACAATCCTGAAGTTTGATTACGAT
      N  I  V  E  S  Q  A  L  S  C  R  V  R  I  S  P  L  L  S  D  S  N  A  S  S  Q  Q  R  L  N  E  D  T  I  V  K  F  D  Y  D

1801  CAATCTCCGCTCCGGGACTACCTAAATAAAAGCCCAGAAAGGACCACTTTGTCTAGCTGGGGCTTCTAAAACGATGCTATTGTGAACAACTTTGCTTCATTCCTCCTACAAAGGGT
      E  S  P  L  R  D  Y  L  N  K  R  P  E  R  T  F  F  V  G  G  A  S  K  N  D  A  I  V  K  K  F  A  Q  V  I  G  A  T  K  G

1921  AATTTTAGGCTAGAATCACCAAACTCATCGTCCCCTTCGTTGGTTCATGTTCATTGTTGTCATTGTTATATCACTCTAATAAAATTGCAGTTCCTTTTGATAAATTCTGAATGACAAT
      N  F  R  L  E  T  P  N  S  C  A  L  G  C  C  Y  K  A  M  W  S  L  L  Y  D  S  N  K  I  A  V  P  F  F  D  K  F  L  N  D  N

2041  TTTTCCATGGCATCTAATGAAAGCATATCCGATTCTGATAATGCAAGATTCTCCCCTTAAGCGAACTCGAAAACACTCTCATCTAAAATATGTTTCAAT
      F  P  W  H  V  M  E  S  I  S  D  V  D  N  E  N  W  I  A  I  I  P  R  L  S  P

2161  AATTTATCATGCCCTGACAAGTACACACAGACACATAATACACATATATATATATCACCGTTATTATGCCGTGCACATGACAATCCCCTTGTATGTTTCGTATACTCTACC

2281  AACTACTCATCATTTGTTCTCCCCGTTTCCCAAAATCACCAAAATAACAAAAAACAATTTATGCAAACCCTCAGCCAACCACCAGACACAACAAATCAAATTA

2401  GCGCCTTTCCACGTCAGAATATAAGACACCATTCAAAGAGCCTAGGTTATTGTTAAATCATCTCCAGCTC
```

*Fig. 2b* pLSK15

Construction of pKS(−)-KK-AR-KD plasmids
* The XhoI site was regenerated after ligation.

Direct amplification of the intact xylitol dehydrogenase gene and the promoterless XD from P. stipitis chromosomal DNA by polymerase chain reaction (PCR) technique.

1. Molecular markers BamHI-EcoRI digested λ DNA.
2. Pichia xylitol dehydrogenase gene (intact).
3. Pichia xylitol dehydrogenase gene (promoterless).
4. Molecular markers, HaeIII digested ΦX DNA.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2467 base pairs
        ( B ) TYPE: Nucleic Acid Sequence
        ( C ) STRANDEDNESS: Double
        ( D ) TOPOLOGY: Linear ( i i ) MOLECULE TYPE: Genomic DNA ( x i ) SEQUENCE DESCRIPTION: SEQ ID NO:1:

```
GGATCCAAGA CCATTATTCC ATCAGAATGG AAAAAAGTTT AAAAGATCAC                    50

GGAGATTTTG TTCTTCTGAG CTTCTGCTGT CCTTGAAAAC AAATTATTCC                   100

GCTGGCCGCC CCAAACAAAA ACAACCCCGA TTTAATAACA TTGTCACAGT                   150

ATTAGAAATT TTCTTTTTAC AAATTACCAT TTCCAGCTTA CTACTTCCTA                   200

TAATCCTCAA TCTTCAGCAA GCGACGCAGG GAATAGCCGC TGAGGTGCAT                   250

AACTGTCACT TTTCAATTCG GCCAATGCAA TCTCAGGCGG ACGAATAAGG                   300

GGGCCCTCTC GAGAAAAACA AAAGGAGGAT GAGATTAGTA CTTTA ATG TTG                351
                                                  Met Leu
                                                   1

TGT TCA GTA ATT CAG AGA CAG ACA AGA GAG GTT TCC AAC ACA                  393
Cys Ser Val Ile Gln Arg Gln Thr Arg Glu Val Ser Asn Thr
         5               10                  15

ATG TCT TTA GAC TCA TAC TAT CTT GGG TTT GAT CTT TCG ACC                  435
Met Ser Leu Asp Ser Tyr Tyr Leu Gly Phe Asp Leu Ser Thr
             20              25                  30

CAA CAA CTG AAA TGT CTC GCC ATT AAC CAG GAC CTA AAA ATT                  477
Gln Gln Leu Lys Cys Leu Ala Ile Asn Gln Asp Leu Lys Ile
                 35              40

GTC CAT TCA GAA ACA GTG GAA TTT GAA AAG GAT CTT CCG CAT                  519
Val His Ser Glu Thr Val Glu Phe Glu Lys Asp Leu Pro His
45               50                  55

TAT CAC ACA AAG AAG GGT GTC TAT ATA CAC GGC GAC ACT ATC                  561
Tyr His Thr Lys Lys Gly Val Tyr Ile His Gly Asp Thr Ile
        60              65                  70

GAA TGT CCC GTA GCC ATG TGG TTA GGG GCT CTA GAT CTG GTT                  603
Glu Cys Pro Val Ala Met Trp Leu Gly Ala Leu Asp Leu Val
            75              80                  85

CTC TCG AAA TAT CGC GAG GCT AAA TTT CCA TTG AAC AAA GTT                  645
Leu Ser Lys Tyr Arg Glu Ala Lys Phe Pro Leu Asn Lys Val
                90              95                 100

ATG GCC GTC TCA GGG TCC TGC CAG CAG CAC GGG TCT GTC TAC                  687
Met Ala Val Ser Gly Ser Cys Gln Gln His Gly Ser Val Tyr
                    105             110

TGG TCC TCC CAA GCC GAA TCT CTG TTA GAG CAA TTG AAT AAG                  729
Trp Ser Ser Gln Ala Glu Ser Leu Leu Glu Gln Leu Asn Lys
115                 120                 125

AAA CCG GAA AAA GAT TTA TTG CAC TAC GTG AGC TCT GTA GCA                  771
Lys Pro Glu Lys Asp Leu Leu His Tyr Val Ser Ser Val Ala
        130                 135                 140

TTT GCA AGG CAA ACC GCC CCC AAT TGG CAA GAC CAC AGT ACT                  813
Phe Ala Arg Gln Thr Ala Pro Asn Trp Gln Asp His Ser Thr
            145                 150                 155
```

```
GCA AAG CAA TGT CAA GAG TTT GAA GAG TGC ATA GGT GGG CCT           855
Ala Lys Gln Cys Gln Glu Phe Glu Glu Cys Ile Gly Gly Pro
            160                 165                 170

GAA AAA ATG GCT CAA TTA ACA GGG TCC AGA GCC CAT TTT AGA           897
Glu Lys Met Ala Gln Leu Thr Gly Ser Arg Ala His Phe Arg
            175                 180

TTT ACT GGT CCT CAA ATT CTG AAA ATT GCA CAA TTA GAA CCA           939
Phe Thr Gly Pro Gln Ile Leu Lys Ile Ala Gln Leu Glu Pro
185                 190                 195

GAA GCT TAC GAA AAA ACA AAG ACC ATT TCT TTA GTG TCT AAT           981
Glu Ala Tyr Glu Lys Thr Lys Thr Ile Ser Leu Val Ser Asn
    200                 205                 210

TTT TTG ACT TCT ATC TTA GTG GGC CAT CTT GTT GAA TTA GAG          1023
Phe Leu Thr Ser Ile Leu Val Gly His Leu Val Glu Leu Glu
            215                 220                 225

GAG GCA GAT GCC TGT GGT ATG AAC CTT TAT GAT ATA CGT GAA          1065
Glu Ala Asp Ala Cys Gly Met Asn Leu Tyr Asp Ile Arg Glu
            230                 235                 240

AGA AAA TTC ATG TAT GAG CTA CTA CAT CTA ATT GAT AGT TCT          1107
Arg Lys Phe Met Tyr Glu Leu Leu His Leu Ile Asp Ser Ser
            245                 250

TCT AAG GAT AAA ACT ATC AGA CAA AAA TTA ATG AGA GCA CCC          1149
Ser Lys Asp Lys Thr Ile Arg Gln Lys Leu Met Arg Ala Pro
255                 260                 265

ATG AAA AAT TTG ATA GCG GGT ACCA TCT GTA AA TAT TTT ATT          1191
Met Lys Asn Leu Ile Ala Gly Thr Ile Cys Lys Tyr Phe Ile
270                 275                 280

GAG AAG TAC GGT TTC AAT ACA AAC TGC AAG GTC TCT CCC ATG          1233
Glu Lys Tyr Gly Phe Asn Thr Asn Cys Lys Val Ser Pro Met
            285                 290                 295

ACT GGG GAT ATT TTA GCC ACT ATA TGT TCT TTA CCC CTG CGG          1275
Thr Gly Asp Asn Leu Ala Thr Ile Cys Ser Leu Pro Leu Arg
            300                 305                 310

AAG AAT GAC GTT CTC GTT TCC CTA GGA ACA AGT ACT ACA GTT          1317
Lys Asn Asp Val Leu Val Ser Leu Gly Thr Ser Thr Thr Val
            315                 320

CTT CTG GTC ACC GAT AAG TAT CAC CCC TCT CCG AAC TAT CAT          1359
Leu Leu Val Thr Asp Lys Tyr His Pro Ser Pro Asn Tyr His
325                 330                 335

CTT TTC ATT CAT CCA ACT CTG CCA AAC CAT TAT ATG GGT ATG          1401
Leu Phe Ile His Pro Thr Leu Pro Asn His Tyr Met Gly Met
340                 345                 350

ATT TGT TAT TGT AAT GGT TCT TTG GCA AGG GAG AGG ATA AGA          1443
Ile Cys Tyr Cys Asn Gly Ser Leu Ala Arg Glu Arg Ile Arg
            355                 360                 365

GAC GAG TTA AAC AAA GAA CGG GAA AAT AAT TAT GAG AAG ACT          1485
Asp Glu Leu Asn Lys Glu Arg Glu Asn Asn Tyr Glu Lys Thr
            370                 375                 380

AAC GAT TGG ACT CTT TTT AAT CAA GCT GTG CTA GAT GAC TCA          1527
Asn Asp Trp Thr Leu Phe Asn Gln Ala Val Leu Asp Asp Ser
            385                 390

GAA AGT AGT GAA AAT GAA TTA GGT GTA TAT TTT CCT CTG GGG          1569
Glu Ser Ser Glu Asn Glu Leu Gly Val Tyr Phe Pro Leu Gly
395                 400                 405

GAG ATC GTT CCT AGC GTA AAA GCC ATA AAC AAA AGG GTT ATC          1611
Glu Ile Val Pro Ser Val Lys Ala Ile Asn Lys Arg Val Ile
    410                 415                 420

TTC AAT CCA AAA ACG GGT ATG ATT GAA AGA GAG GTG GCC AAG          1653
Phe Asn Pro Lys Thr Gly Met Ile Glu Arg Glu Val Ala Lys
            425                 430                 435
```

| | | | | | | | | | | | | | |
|---|---|---|---|---|---|---|---|---|---|---|---|---|---|
| TTC | AAA | GAC | AAG | AGG | CAC | GAT | GCC | AAA | AAT | ATT | GTA | GAA | TCA | 1695 |
| Phe | Lys | Asp | Lys | Arg | His | Asp | Ala | Lys | Asn | Ile | Val | Glu | Ser |
| | | | 440 | | | | | 445 | | | | | 450 |

| CAG | GCT | TTA | AGT | TGC | AGG | GTA | AGA | ATA | TCT | CCC | CTG | CTT | TCG | 1737 |
|---|---|---|---|---|---|---|---|---|---|---|---|---|---|---|
| Gln | Ala | Leu | Ser | Cys | Arg | Val | Arg | Ile | Ser | Pro | Leu | Leu | Ser |
| | | | | 455 | | | | | 460 | | | | |

| GAT | TCA | AAC | GCA | AGC | TCA | CAA | CAG | AGA | CTG | AAC | GAA | GAT | ACA | 1779 |
|---|---|---|---|---|---|---|---|---|---|---|---|---|---|---|
| Asp | Ser | Asn | Ala | Ser | Ser | Gln | Gln | Arg | Leu | Asn | Glu | Asp | Thr |
| 465 | | | | | 470 | | | | | 475 | | | |

| ATC | GTG | AAG | TTT | GAT | TAC | GAT | GAA | TCT | CCG | CTG | CGG | GAC | TAC | 1821 |
|---|---|---|---|---|---|---|---|---|---|---|---|---|---|---|
| Ile | Val | Lys | Phe | Asp | Tyr | Asp | Glu | Ser | Pro | Leu | Arg | Asp | Tyr |
| | 480 | | | | | 485 | | | | | 490 | | |

| CTA | AAT | AAA | AGG | CCA | GAA | AGG | ACT | TTT | TTT | GTA | GGT | GGG | GCT | 1863 |
|---|---|---|---|---|---|---|---|---|---|---|---|---|---|---|
| Leu | Asn | Lys | Arg | Pro | Glu | Arg | Thr | Phe | Phe | Val | Gly | Gly | Ala |
| | | 495 | | | | | 500 | | | | | 505 | |

| TCT | AAA | AAC | GAT | GCT | ATT | GTG | AAG | AAG | TTT | GCT | CAA | GTC | ATT | 1905 |
|---|---|---|---|---|---|---|---|---|---|---|---|---|---|---|
| Ser | Lys | Asn | Asp | Ala | Ile | Val | Lys | Lys | Phe | Ala | Gln | Val | Ile |
| | | | 510 | | | | | 515 | | | | | 520 |

| GGT | GCT | ACA | AAG | GGT | AAT | TTT | AGG | CTA | GAA | ACA | CCA | AAC | TCA | 1947 |
|---|---|---|---|---|---|---|---|---|---|---|---|---|---|---|
| Gly | Ala | Thr | Lys | Gly | Asn | Phe | Arg | Leu | Glu | Thr | Pro | Asn | Ser |
| | | | | 525 | | | | | 530 | | | | |

| TGT | GCC | CTT | GGT | GGT | TGT | TAT | AAG | GCC | ATG | TGG | TCA | TTG | TTA | 1989 |
|---|---|---|---|---|---|---|---|---|---|---|---|---|---|---|
| Cys | Ala | Leu | Gly | Gly | Cys | Tyr | Lys | Ala | Met | Trp | Ser | Leu | Leu |
| 535 | | | | | 540 | | | | | 545 | | | |

| TAT | GAC | TCT | AAT | AAA | ATT | GCA | GTT | CCT | TTT | GAT | AAA | TTT | CTG | 2031 |
|---|---|---|---|---|---|---|---|---|---|---|---|---|---|---|
| Tyr | Asp | Ser | Asn | Lys | Ile | Ala | Val | Pro | Phe | Asp | Lys | Phe | Leu |
| 550 | | | | | 555 | | | | | 560 | | | |

| AAT | GAC | AAT | TTT | CCA | TGG | CAT | GTA | ATG | GAA | AGC | ATA | TCC | GAT | 2073 |
|---|---|---|---|---|---|---|---|---|---|---|---|---|---|---|
| Asn | Asp | Asn | Phe | Pro | Trp | His | Val | Met | Glu | Ser | Ile | Ser | Asp |
| | | 565 | | | | | 570 | | | | | 575 | |

| GTG | GAT | AAT | GAA | AAT | TGG | ATC | GCT | ATA | ATT | CCA | AGA | TTG | TCC | 2115 |
|---|---|---|---|---|---|---|---|---|---|---|---|---|---|---|
| Val | Asp | Asn | Glu | Asn | Trp | Ile | Ala | Ile | Ile | Pro | Arg | Leu | Ser |
| | | | 580 | | | | | 585 | | | | | 590 |

| CCT | TAAGCGAACT | GGAAAAGACT | CTCATCTAAA | ATATGTTTGA | ATAATTTATC | 2168 |
|---|---|---|---|---|---|---|
| Pro | | | | | | |

| ATGCCCTGAC | AAGTACACAC | AAACACAGAC | ACATAATATA | CATACATATA | 2218 |
|---|---|---|---|---|---|
| TATATATCAC | CGTTATTATG | CGTGCACATG | ACAATGCCCT | TGTATGTTTC | 2268 |
| GTATACTGTA | GCAAGTAGTC | ATCATTTGT | TCCCCGTTCG | GAAAATGACA | 2318 |
| AAAAGTAAAA | TCAATAAATG | AAGAGTAAAA | AACAATTTAT | GAAAGGGTGA | 2368 |
| GCGACCAGCA | ACGAGAGAGA | CAAATCAAAT | TAGCGCTTTC | CAGTGAGAAT | 2418 |
| ATAAGAGAGC | ATTGAAAGAG | CTAGGTTATT | GTTAAATCAT | CTCGAGCTC | 2467 |

( 2 ) INFORMATION FOR SEQ ID NO:2:

( i ) SEQUENCE CHARACTERISTICS:
        ( A ) LENGTH: 19 bases
        ( B ) TYPE: Nucleotide Sequence
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO:2:

TCTAGACCAC CCTAAGTCG                                    19

( 2 ) INFORMATION FOR SEQ ID NO:3:

( i ) SEQUENCE CHARACTERISTICS:
        ( A ) LENGTH: 16 bases
        ( B ) TYPE: Nucleotide Sequence

```
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO:3:

CACACAATTA AAATGA                                                          16

( 2 ) INFORMATION FOR SEQ ID NO:4:

( i ) SEQUENCE CHARACTERISTICS:
        ( A ) LENGTH: 19 bases
        ( B ) TYPE: Nucleotide Sequence
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO:4:

GGATCCACTA TAGTCGAAG                                                       19
```

RECOMBINANT YEASTS FOR EFFECTIVE FERMENTATION OF GLUCOSE AND XYLOSE

BACKGROUND OF THE INVENTION

The present invention relates generally to genetically engineered yeasts capable of simultaneously fermenting the two major sugar constituents of cellulosic biomass, glucose and xylose, to ethanol. More particularly, the present invention relates to such yeasts which can be constructed by cloning a xylose reductase gene, a xylitol dehydrogenase gene, and a xylulokinase gene in yeasts capable of fermenting glucose to ethanol.

Recent studies have proven ethanol to be an ideal liquid fuel for automobiles. It can be used directly as a neat fuel (100% ethanol) or as a blend with gasoline at various concentrations.

The use of ethanol to supplement or replace gasoline can reduce the dependency of many nations on imported foreign oil and also provide a renewable fuel for transportation. Furthermore, ethanol has proven a cleaner fuel that releases far less pollutants into the environment than regular gasoline. For example, it has been demonstrated that the use of oxygenated materials in gasoline can reduce the emission of carbon monoxide, a harmful pollutant, into the air. Among the several oxygenates currently used for boosting the oxygen content of gasoline, ethanol has the highest oxygen content. The United States Environmental Protection Agency (EPA) has shown that gasoline blended with 10% ethanol reduces carbon monoxide emissions by about 25%–30%.

Up to now, the feedstock used for the production of industrial alcohol by fermentation has been sugars from sugar cane or beets, starch from corn or other food crops. However, these agricultural crops are too expensive to be used as feedstock for the large-scale production of fuel ethanol.

Plant biomass is an attractive feedstock for ethanol-fuel production by fermentation because it is renewable, and available at low cost and in large amounts. The concept of using alcohol produced by microbial fermentation of sugars from agricultural biomass had its nascense at least two decades ago. The major fermentable sugars from cellulosic materials are glucose and xylose (with the ratio of glucose to xylose being approximately 2 or 3 to 1). The most desirable fermentations of cellulosic materials would, of course, completely convert both glucose and xylose to ethanol. Unfortunately, even now there is not a single natural known microorganism capable of fermenting both glucose and xylose effectively.

Yeasts, particularly Saccharomyces, have traditionally been used for fermenting glucose-based feedstocks to ethanol, and they are still the best microorganisms for converting glucose to ethanol. However, these glucose-fermenting yeasts have been found not only unable to ferment xylose but also unable to use the pentose sugar for growth. Nevertheless, these glucose-fermenting yeasts can use xylulose for growth and fermentation (FIG. 1), albeit with varying efficacy. For example, *S. cerevisiae* ferments xylulose very poorly while species of Schizosaccharomyces does so quite effectively (Chiang et al., 1981; Lastick et al., 1989).

Even though the glucose-fermenting yeasts are unable to use xylose both for growth and fermentation, there are many natural yeasts that can use xylose for growth aerobically but they cannot ferment xylose to ethanol. These xylose-using/non-fermenting yeasts rely upon two enzymes—xylose reductase and xylitol dehydrogenase—to convert xylose to xylulose. These yeasts are different from most bacteria which rely on a single enzyme—xylose isomerase—to convert xylose directly to xylulose (FIG. 1). The yeast xylose reductase and xylitol dehydrogenase also require cofactors for their actions; xylose reductase depends on NADPH as its cofactor and xylitol dehydrogenase depends on NAD as its cofactor. On the contrary, bacterial xylose isomerase requires no cofactor for direct conversion of xylose to xylulose (FIG. 1).

Two decades ago, much effort was devoted in an attempt to find new yeasts capable of effectively fermenting both glucose and xylose to ethanol. Although no such ideal yeast has been found, those efforts did have limited success. For example, a few yeasts were found to be capable not only of utilizing xylose for growth aerobically, but also of fermenting xylose to ethanol (Toivola et al., 1984; Dupreez and vander Walt, 1983), although none of these xylose-fermenting yeasts were totally effective in fermenting xylose to ethanol (Jeffries, 1985). In addition, these yeasts are unable to ferment glucose effectively.

Among the xylose-fermenting yeasts, three species, *Pachysolen tannophilus* (Toivola et al., 1984), *Candida shehatae* (Dupreez and van der Walt, 1983), and *Pichia stipitis* (Grootjen et al., 1990) have been extensively characterized. *P. stipitis* and *C. shihatae* ferment xylose better than other xylose-fermenting yeasts (Grootjen et al., 1990). Nevertheless, even the best xylose-fermenting yeasts lack high efficiency in fermenting xylose, and are also highly ineffective in fermenting glucose (Jeffries, 1985).

In the past decade, efforts were also made to genetically modify traditional glucose-fermenting yeasts, particularly *S. cerevisiae*, by recombinant DNA techniques. Initial efforts were concentrated on cloning a xylose isomerase gene into yeast to render it capable of converting xylose directly to xylulose without dependence on cofactors. However, these efforts have been unsuccessful because the genes encoding various bacterial xylose isomerases are incapable of directing the synthesis of an active enzyme in *S. cerevisiae* (Rosenfeld et al., 1984; Ho et al., 1983; Sarthy et al., 1987; Wilhelm and Hollenberg, 1984; Amore et al., 1989)).

In the last few years, efforts toward genetically engineering yeasts, particularly *S. cerevisiae*, to ferment xylose have been focused on cloning genes encoding xylose reductase (Takama et al., 1991; Hallborn et al., 1991; Strasser et al., 1990), xylitol dehydrogenase (Koetter et al., 1990; Hallborn et al., 1990), and xylulokinase (Stevis et al., 1987; Chang and Ho, 1988; Ho and Chang, 1989; Deng and Ho, 1990). *S. cerevisiae* and other glucose-fermenting yeasts do not contain any detectable xylose reductase or xylitol dehydrogenase activities, but all seem to contain xylulokinase activity. Thus, the glucose-fermenting yeasts can all ferment xylulose, but do so with varying efficacy (Deng and Ho, 1990).

Recently, Koetter et al. (1990), Strasser et al. (1990), and Hallborn et al. (1990; 1991), have cloned both the xylose reductase and the xylitol dehydrogenase gene in *S. cerevisiae*. However, these genetically engineered yeasts still cannot effectively ferment xylose. For example, these yeasts have been incapable of fermenting more than 2% xylose. In addition, they produce large amounts of xylitol from xylose (Hallborn et al., 1990; Koetter and Ciriacy, 1993), which diverts the valuable xylose substrate from the desired fermentive path to ethanol.

The extensive background in this field as outlined above demonstrates that despite the concerted and longstanding efforts of numerous researchers, yeasts capable of effectively fermenting both glucose and xylose to ethanol have not been achieved. Accordingly, there remain needs for such yeasts and for methods of their preparation and use. It is to these needs that the present invention is addressed.

SUMMARY OF THE INVENTION

A feature of this invention relates to the discovery that new yeast strains capable of effectively fermenting xylose alone or simultaneously with glucose can be created using recombinant DNA and gene cloning techniques. Particularly, these techniques have been used to create new recombinant yeasts containing cloned xylose reductase (XR), xylitol dehydrogenase (XD), and xylulokinase (XK) genes which are fused to promotors not inhibited by the presence of glucose.

Accordingly, one preferred embodiment of the invention provides a recombinant yeast strain containing introduced genes encoding xylose reductase, xylitol dehydrogenase and xylulokinase and capable of fermenting xylose to ethanol. The recombinant yeast strain is preferably also capable of fermenting glucose to ethanol, and more preferred such yeast strains which can effectively ferment these two sugars simultaneously to ethanol are achieved where the XR, XD and XK genes are fused to promotors which are not inhibited by the presence of glucose and also do not require xylose for induction.

Another preferred embodiment of the invention provides a recombinant yeast strain containing genes encoding xylose reductase, xylitol dehydrogenase and xylulokinase, wherein said genes are fused to non-glucose-inhibited promoters and wherein said yeast is capable of fermenting xylose to ethanol. The recombinant yeast strain is preferably also capable of fermenting glucose to ethanol.

Other preferred embodiments of the invention relate to reagents useful for the production of recombinant yeasts of the invention. Thus, the present invention also provides a recombinant DNA molecule comprising genes encoding xylose reductase, xylitol dehydrogenase, and xylulokinase. As well, the invention provides a vector comprising genes encoding xylose reductase, xylitol dehydrogenase and xylulokinase. In these reagents, the genes are preferably fused to promoters which are not inhibited by glucose and also do not require xylose for induction, so as to enable the expedient production of recombinant yeasts capable of simultaneously fermenting glucose and xylose to ethanol.

Another preferred embodiment of the present invention provides a method for obtaining a recombinant yeast capable of fermenting xylose to ethanol. This method includes the step of introducing DNA into a yeast so as to cause the yeast to have introduced genes encoding xylose reductase, xylitol dehydrogenase and xylulokinase. Preferably, these genes will be fused to non-glucose-inhibited promotors to enable simultaneous fermentation of glucose and xylose to ethanol. Advantageously, all three genes can be introduced simultaneously, for instance using reagents of the invention as discussed above.

Still other preferred embodiments of the invention provide methods for fermenting xylose or glucose to ethanol. The inventive methods include the step of fermenting a xylose-containing or glucose-containing medium with a recombinant yeast strain containing introduced genes encoding xylose reductase, xylitol dehydrogenase and xyluloki- nase. It is desirable that the three introduced genes be fused to non-glucose-inhibited promoters, and that the medium contain both glucose and xylose, so as to provide the concurrent fermentation of xylose and glucose to ethanol.

Additional preferred embodiments, features and advantages of the invention will be apparent from the following description.

BRIEF DESCRIPTION OF THE FIGURES

Figure 2A:
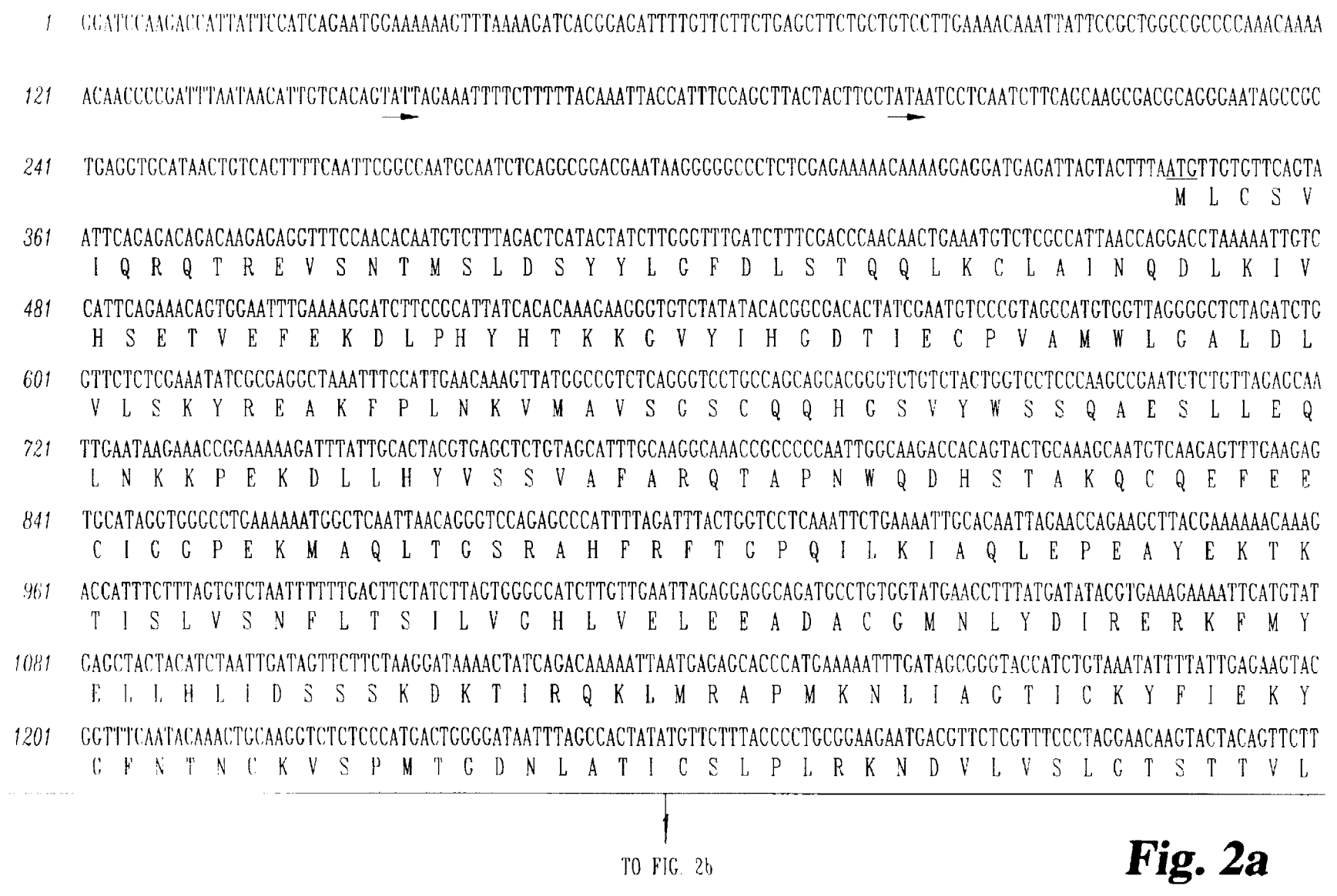

FIG. 2a–b shows the nucleotide sequence and deduced amino acid sequence of the yeast xylulokinase gene including its 5'- and 3'-flanking sequences (Seq. ID. No: 1). The initiation codon and stop codon are underlined. The possible control sequences in the 5' and 3' non-coding regions are indicated by arrows.

DETAILED DESCRIPTION

Figure 1:
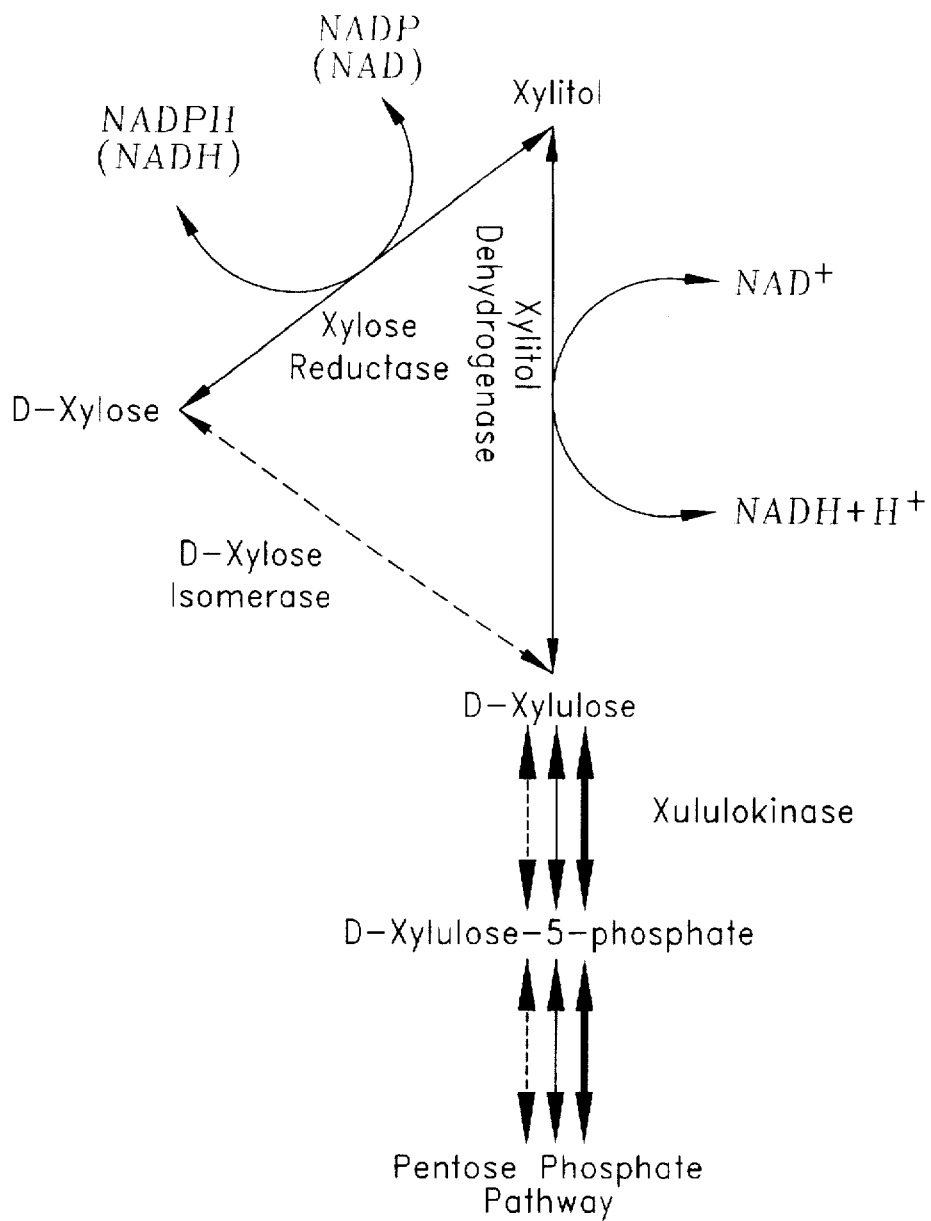
FIG. 1 is a schematic diagram of the enzymes associated with early stages of xylose metabolism in bacteria and yeasts.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention pertains.

The present invention provides recombinant yeasts, DNA molecules and vectors comprising XR, XD and XK genes. Such genes are well known to occur in a wide variety of microorganisms and, in fact, as discussed hereinabove, numerous XR, XD and XK genes have been identified and isolated. The particular source of these genes is not critical to the broad aspects of this invention; rather, any DNAs encoding proteins (enzymes) having xylose reductase activity (the ability to convert D-xylose to xylitol with NADPH or NADH as cofactor), xylitol dehydrogenase activity (the ability to convert xylitol to D-xylulose with AND$^+$ as cofactor), or xylulokinase activity (the ability to convert D-xylulose to D-xylulose-5-phosphate) will be suitable. These genes may be obtained as naturally-occurring genes, or may be modified, for example, by the addition, substitution or deletion of bases to or of the naturally-occurring gene, so long as the encoded protein still has XR, XD or XK activity. Similarly, the genes or portions thereof may be synthetically produced by known techniques, again so long as the resulting DNA encodes a protein exhibiting the desired XR, XD or XK activity.

As examples, suitable sources of XR and XD genes include xylose-utilizing yeasts such as *Candida shehatae*, *Pichia stipitis*, *Pachysolen tannophilus*, suitable sources of XK genes include the above-noted xylose-utilizing yeasts, as well a xylose non-utilizing yeasts such as those from the genus *Saccharomyces*, e.g. *S. cerevisiae*, the genus *Schizosaccharomyces*, e.g. *Schizosaccharomyces pombe*, and bacteria such as *Escherichia coli*, Bacillus species, Streptomyces species, etc. Genes of interest can be recovered from these sources utilizing conventional methodologies. For example, hybridization, complementation or PCR techniques can be employed for this purpose.

The particular XR gene used in the applicants' studies herein was cloned from *P. stipitis* by Polymerase Chain Reaction (PCR) (Chen and Ho, 1993). The oligonucleotides required for the amplification of XR from the chromosomal DNA by PCR were synthesized according to the published sequence of the *P. stipitis* XR gene (Takama et al., 1991). The amplified XR was first cloned and stored into plasmid pUC19. The cloned XR was then fused to different promotors including the promotors of yeast TRP5 gene (Zalkin and Yanofsky, 1982) and yeast alcohol dehydrogenase I gene (ADCl) (Ammerer, 1983; Bennetzen and Hall, 1982).

The XD gene used in the applicants' studies was also cloned from *P. stipitis* by PCR. The oligonucleotides required for the amplification of XD from the Pichia chromosomal DNA were synthesized according to the published sequence of the Pichia XD gene (Köetter et al., 1990). The amplified XD was also first cloned and stored in pUC19. The gene was then subsequently fused to glycolytic promoters of yeast pyruvate kinase gene (PYK) (Burke et al., 1983) and yeast glyceraldehyde 3 phosphodehydrogenase gene (GPD) (Holland and Holland, 1979).

The applicants have cloned three different XK genes, those from *S. cerevisiae* (Ho and Chang, 1989), *P. tannophilus* (Stevis et al., 1987) and *E. coli* and have found that all three genes can be effectively expressed in *S. cerevisiae* after fusion to a highly efficient yeast promoter. The cloned *S. cerevisiae* xylulokinase gene was used in the illustrative work set forth herein. To assist in properly fusing the yeast XK gene to a suitable promoter, the complete nucleotide sequence of the *S. cerevisiae* XK gene including its 5' and 3' non-coding sequence has been analyzed and is shown in FIG. 2.

A wide variety of promotors will be suitable for use in the invention. Broadly speaking, yeast-compatible promotors capable of controlling transcription of the XR, XD or XK genes will be used. Such promotors are available from numerous known sources, including yeasts, bacteria, and other cell sources. Preferably, the promoters used in the invention will be efficient, non-glucose-inhibited promoters, which do not require xylose for induction. In this regard, an "efficient" promotor as used herein refers to a promotor which provides a high level of transcription of the fused gene. Promotors having these characteristics are also widely available, and their use in the present invention, given the teachings herein, will be within the purview of the ordinarily skilled artisan, as will be the fusion of the promoters to the XR, XD and XK genes, the cloning of the promotor/gene fusion products into appropriate vectors and the use of the vectors to transform yeast. All of these manipulations can be performed using conventional genetic engineering techniques well known to the art and literature.

Figure 5:
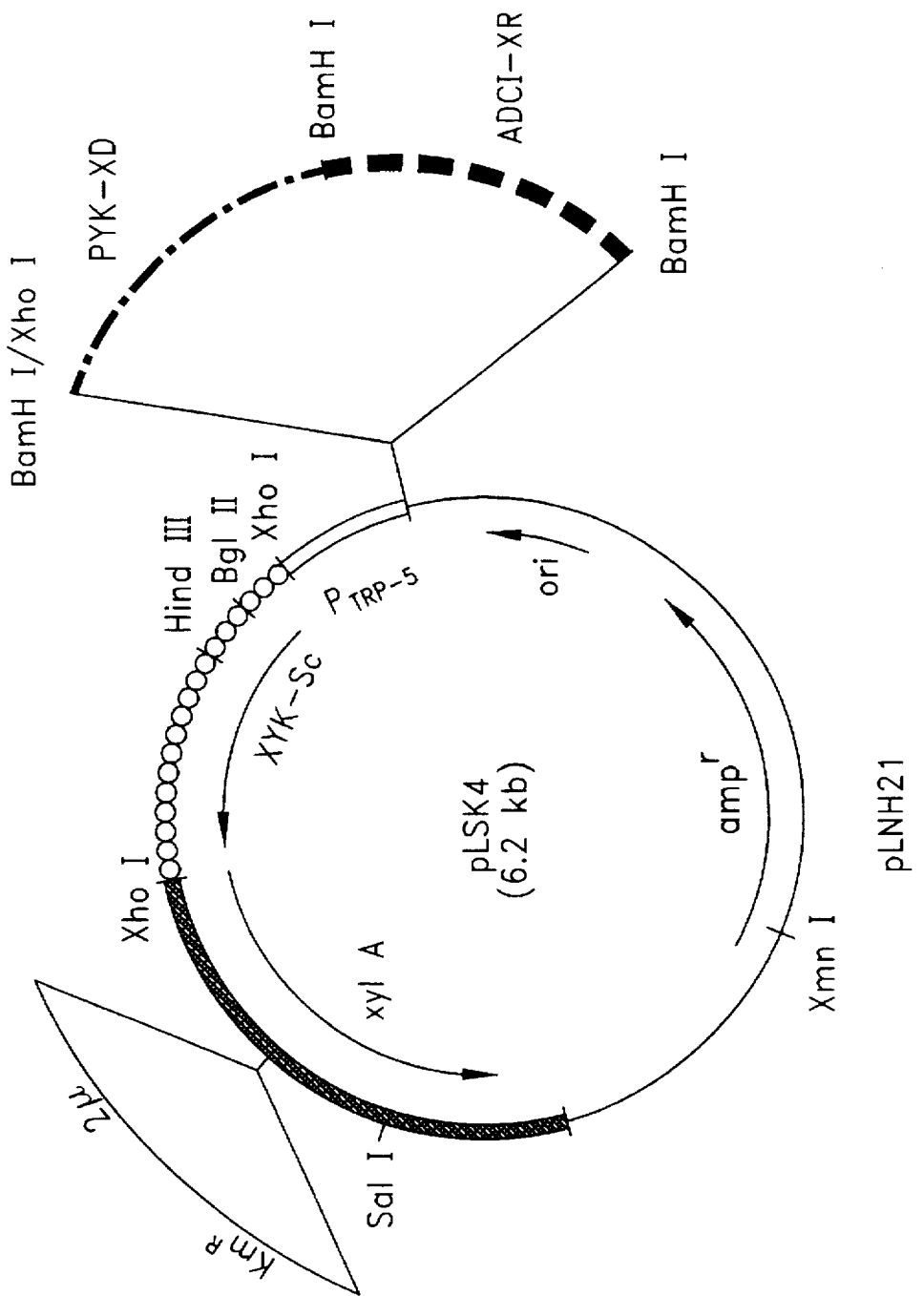
FIG. 5 shows the genes cloned on and the restriction map of the plasmid pLNH21.
Figure 7:
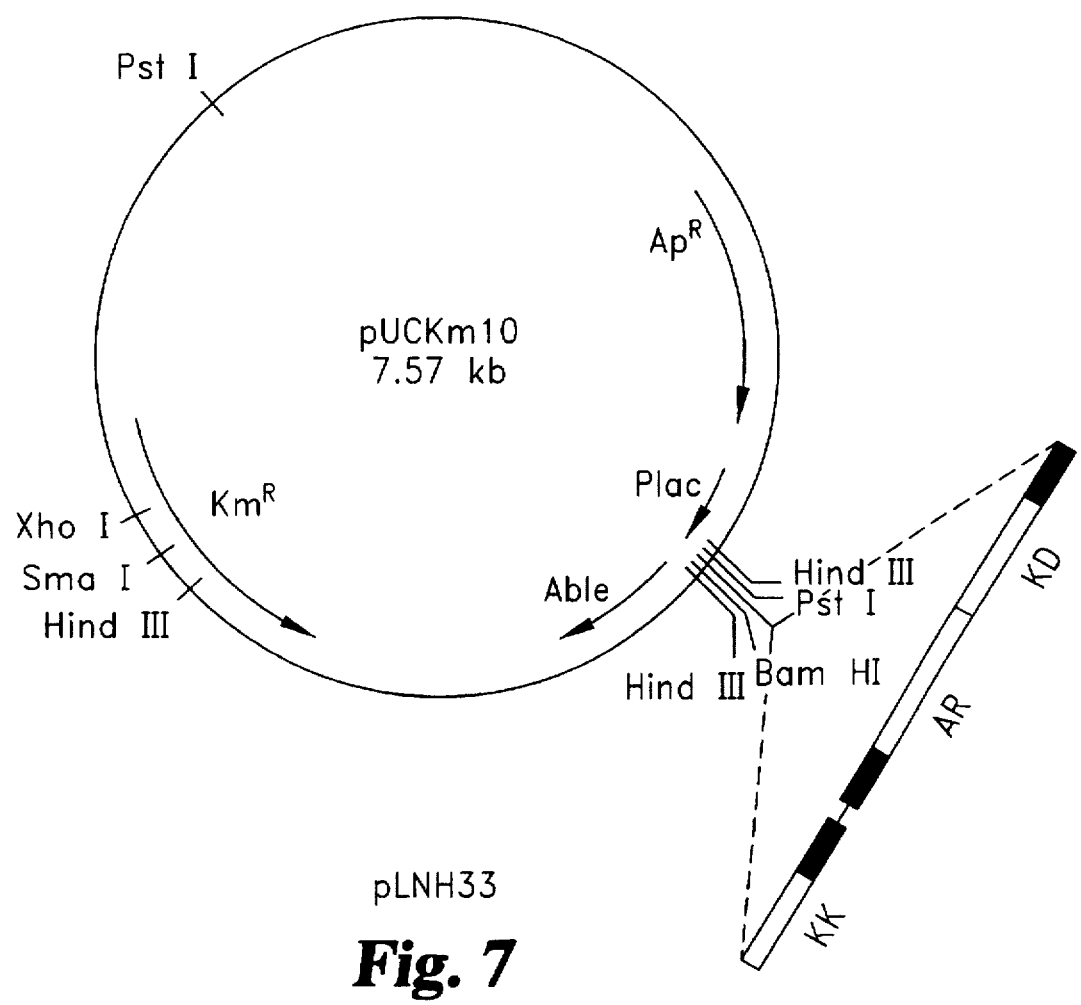
FIG. 7 shows the genes cloned on and the restriction map of plasmid pLNH33.

More particularly describing the applicant's illustrative work herein, the yeast xylulokinase gene, XK, has been fused to promoters from yeast alcohol dehydrogenase gene (ADCl), yeast pyruvate kinase gene (PYK), yeast TRP5-gene, etc. XK fused to the TRP-5 promoter was used to construct pLNH21 (FIG. 5) and XK fused to the PYK promotor was used to construct pLNH33 (FIG. 7).

Figure 9:
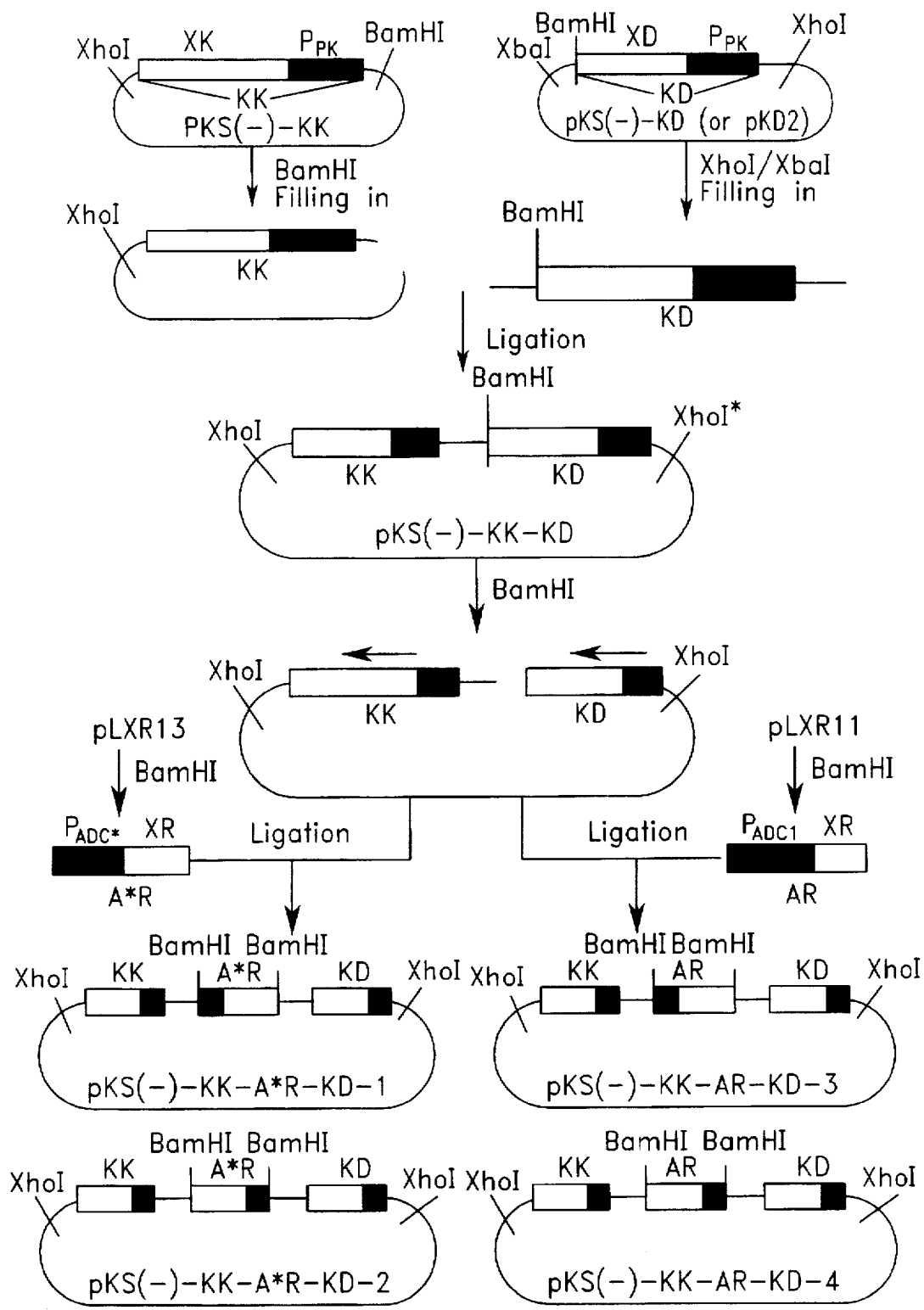
FIG. 9 is a schematic diagram outlining the construction of pBluescript II KS(-) containing the cloned XR, XD, and XK genes: four such plasmids were constructed: pKS(-)-KK-A*R-KD-1; pKS(-)-KK-A*R-KD-2; pKS(-)-KK-AR-KD-3; and pKS(-)-KK-AR-KD-4, as further described in Example 4.

The fusion of XR, XD, and XK to intact promoters from ADCl, PYK, GPD, etc., was carried out by cloning both the fragment containing the specific promoter and the structural gene of XR, XD, or XK on one of the Bluescript KS plasmids (Stratagene, La Jolla, Calif.), followed by the removal of the extra unwanted nucleotides by site-specific mutagenesis (Kunkel et al., 1987). The invention thus also provides several pBluescript II KS(-) (hereinafter pKS(-)) derivatives containing the cloned XD (fused to the pyruvate dehydrogenase promoter), XR (fused to the ADCl promoter), and XK (fused to the pyruvate kinase promoter). These recombinant plasmids are designated as pKS(-) KD-AR (or A*R) -KK. Four such plasmids were constructed as outlined in FIG. 9. These plasmids have similar but not identical structures. The XR, XD, and XK (or KD-AR (or A*R) -KK) cloned on these plasmids can be separated from the parent pKS(-) plasmid by a single XhoI restriction digestion.

Figure 3:
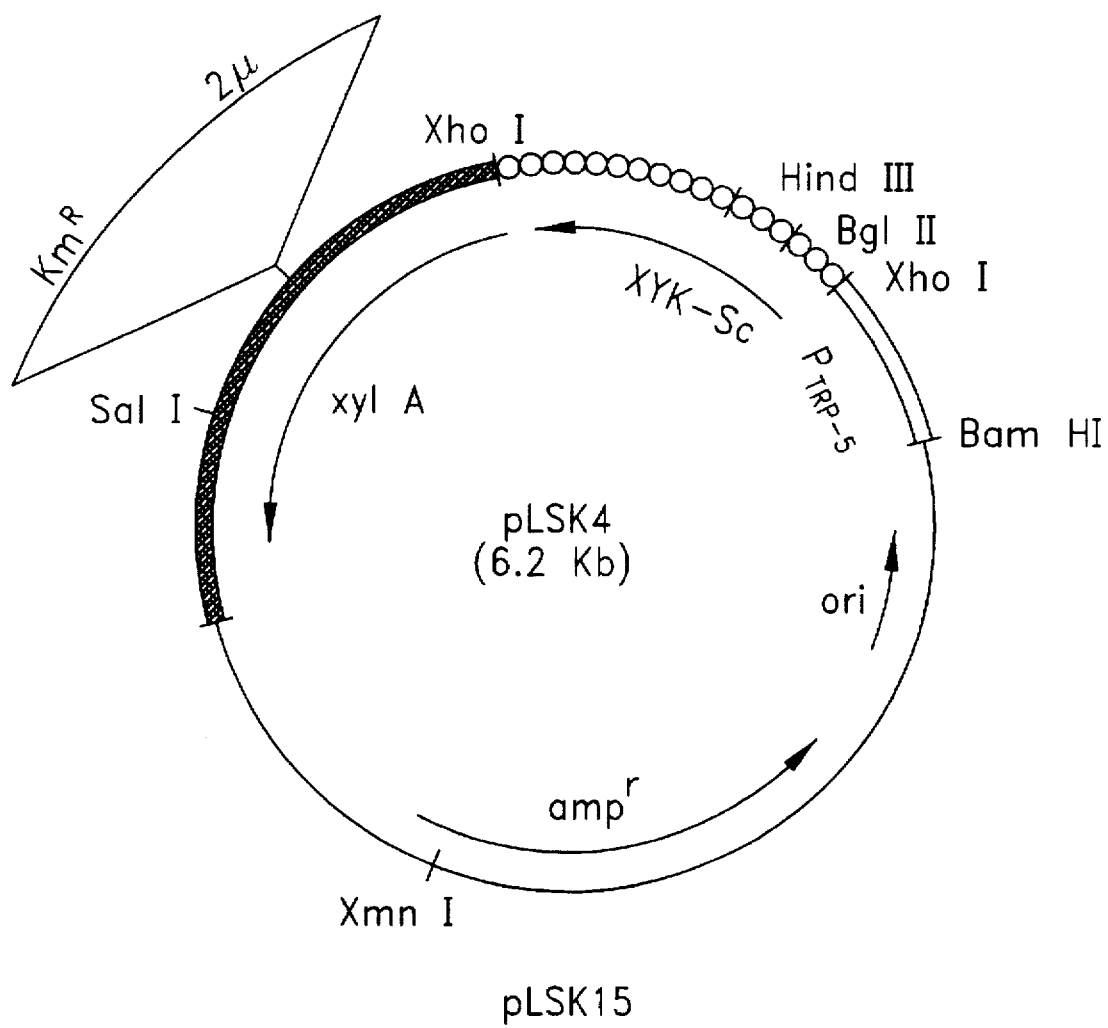
FIG. 3 shows the genes cloned on and the restriction map of the plasmid pLSK15.
Figure 4:
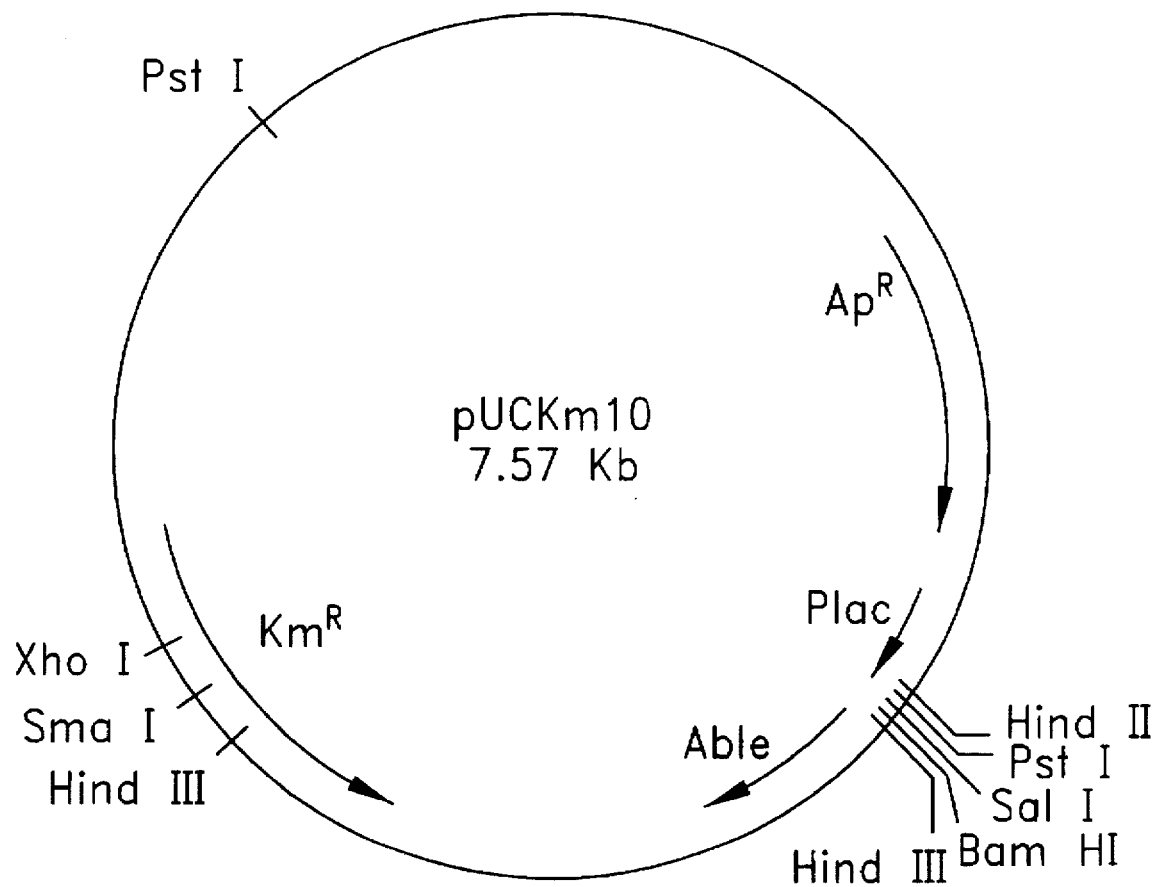
FIG. 4 shows the genes cloned on and the restriction map of the plasmid pUCKm10.
Figure 6A:
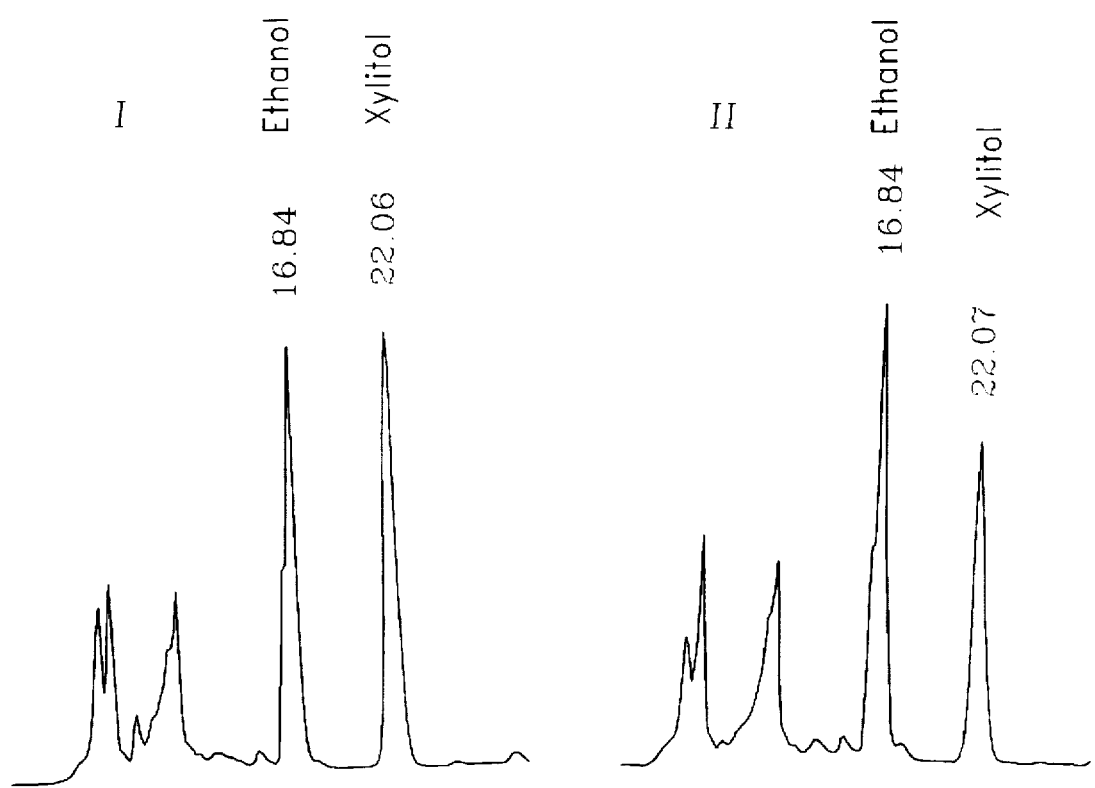
FIG. 6A shows an HPLC chromatogram of a fermentation broth obtained by fermenting xylose with recombinant yeast SC (pLNH21) (*S. cerevisiae* containing introduced XR, XD and XK genes) for (I) 2 days; and (II) 4 days.
Figure 6B:
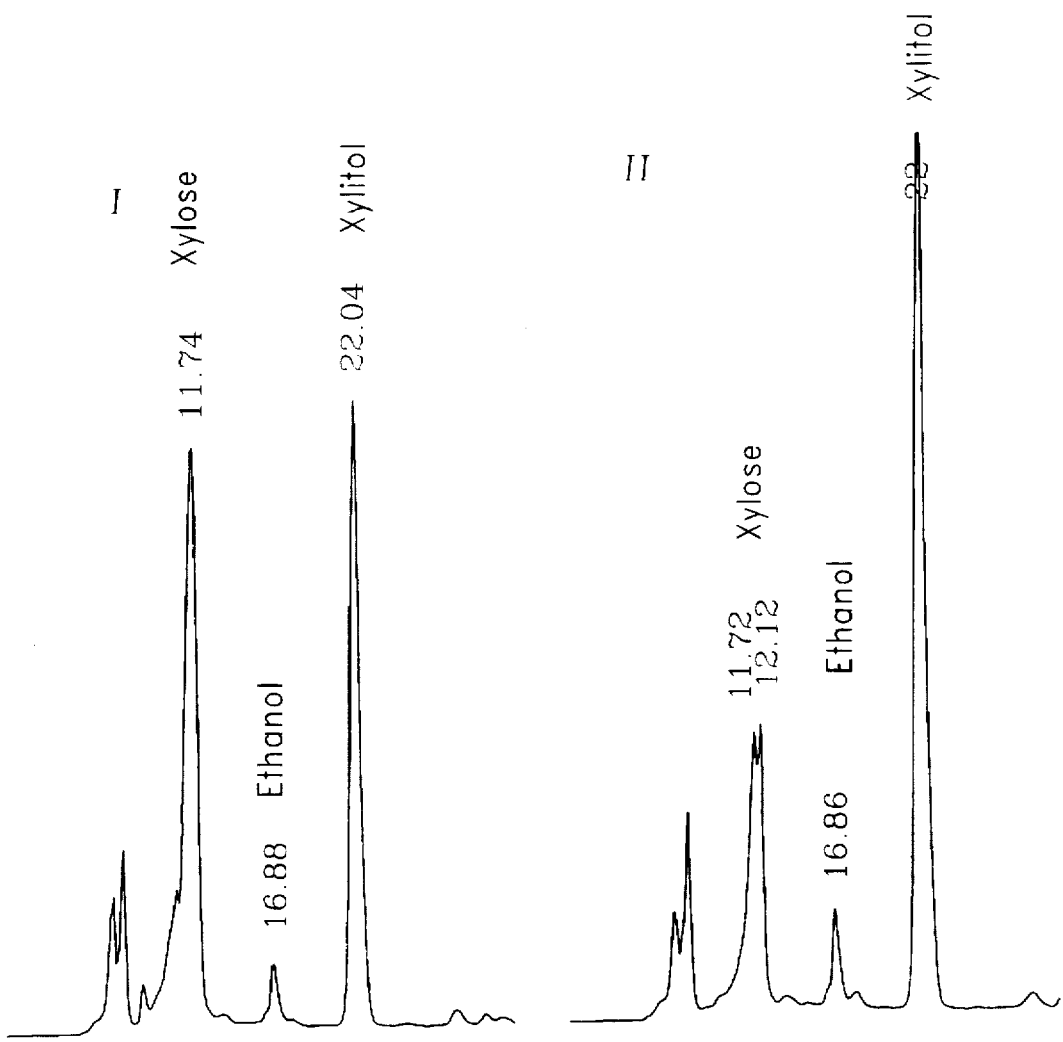
FIG. 6B shows an HPLC chromatogram of a fermentation broth obtained by fermenting xylose with recombinant yeast SC (pLNH13-32) (*S. cerevisiae* containing introduced XR and XD but not XK genes) for (I) 2 days; and (II) 6 days.
Figure 6C:
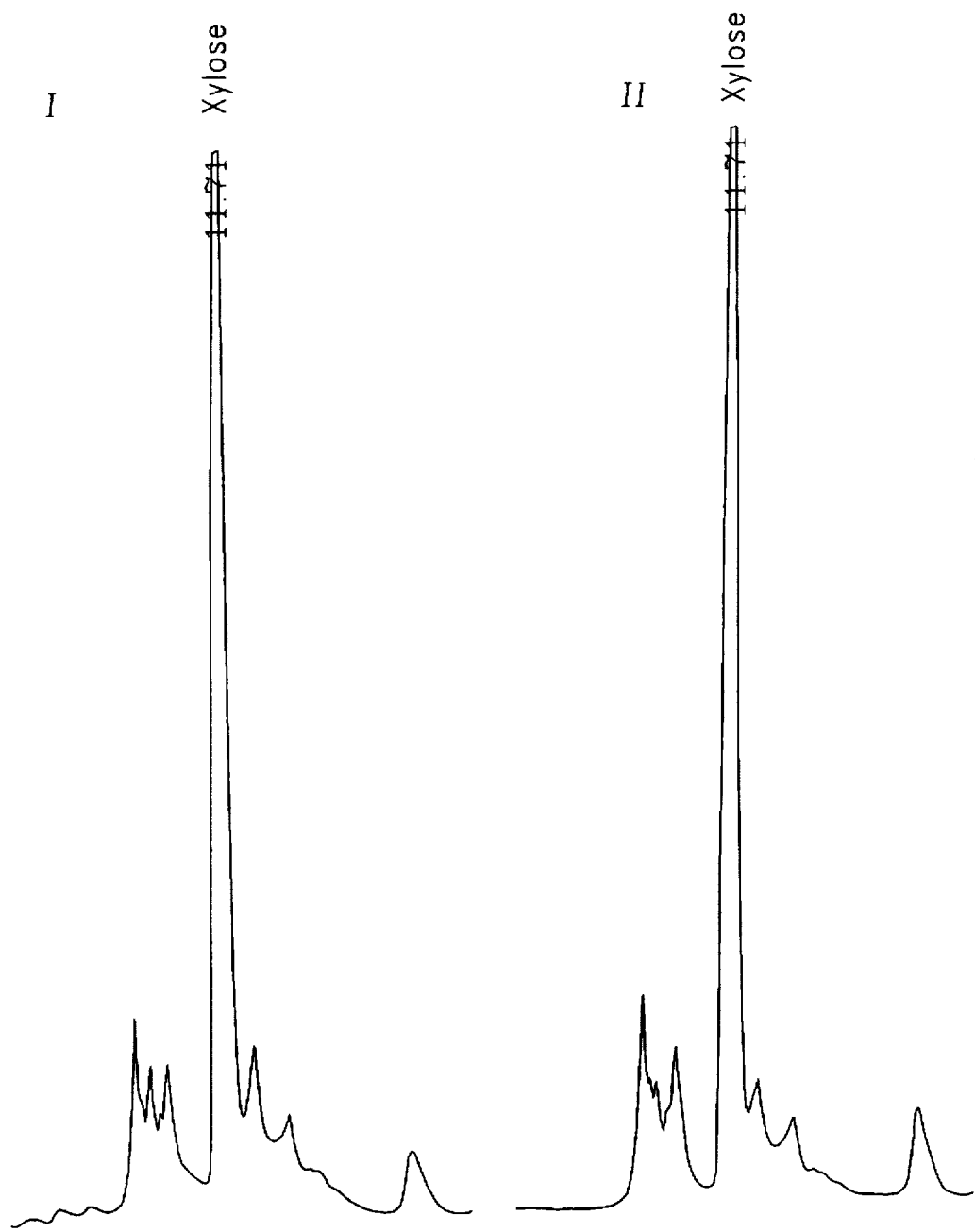
FIG. 6C shows an HPLC chromatogram of a fermentation broth obtained by fermenting xylose with an un-engineered *S. cerevisiae* yeast (containing no introduced XR, XD or XK genes) for (I) 2 days; and (II) 7 days, as further described in Example 6.

The XR, XD, and XK genes fused to the proper promoters were then cloned on pLSK15 (FIG. 3) or pUCKm10 (FIG. 4). pLSK15, a derivative of pLX10-14 (Stevis and Ho, 1985), is a low copy number plasmid with a copy number of approximately 10 in yeast (*S. cerevisiae*). It contains the yeast 2µ replicon which enables the plasmid to be replicated autonomously in *S. cerevisiae* and closely related species. pLSK15 also contains the geneticin (kanamycin) resistance gene (Km$^R$) and ampicillin resistance gene (Ap$^R$ and also amp$^r$) which serve as selection markers in *S. cerevisiae* and other yeasts. pLSK15 also contains the XK gene fused to the yeast TRP-5 promoter. Thus, XR and XD genes fused to proper 5' noncoding sequences containing suitable promoters were inserted into pLSK15 to demonstrate the effect of the resulting plasmids on yeast xylose fermentation. To compare the effect of the presence of different genes on yeast xylose fermentation, a plasmid containing only XR and XD was also used to transform *S. cerevisiae* and the resulting yeast used in comparative fermentations. Results of the fermentation of xylose by un-engineered *S. cerevisiae*, yeast containing the cloned XR, XD, and XK (SC(pLNH21)), and yeast containing the cloned XR and XD but not XK (SC (pLNH13-32)) genes are shown in FIG. 6A, 6B, and 6C.

pUCKm10 (FIG. 4) is a high copy-number plasmid (i.e. plasmid with a copy number of about 50 or more) with a copy number close to 100 in *S. cerevisiae*. pUCKm10 is a pUC9 derivative containing the identical 2µ replicon, and the Km$^R$, and Ap$^R$ genes present in pLSK15. These specific DNA fragments serve as the replicon and selection markers that enable the plasmid to be replicated autonomously in *S. cerevisiae* (and in related yeasts) and also enable the yeast transformants containing the plasmid to be distinguished from the untransformed host cells.

The applicants have constructed pUCKm10 based recombinant plasmids that contain the same XR, XD, and XK fused to 5' proper noncoding sequences containing suitable promotors. These vectors are designed to be useful to transform all *S. cerevisiae* strains and strains of related species. No special mutants are required to act as the recipient strains. Thus plasmids such as pLNH33 (FIG. 7), as well as pLNH21 (FIG. 5), can be used to transform industrial *S. cerevisiae* and other strains.

Yeast transformation with derivatives of either pLSK15 or pUCKm10 was carried out by electroporation generally using the the procedure described by Becker and Guarente (1991). Authentic yeast transformants containing derivatives of either pLSK15 or pUCKm10 were isolated as further described below. Km$^R$ present in the plasmids served as the primary selection marker which renders any host cells obtaining one of these plasmids resistant to a much higher concentration of geneticin present in the medium. However, some yeast cells can be induced to become resistant to the same level of geneticin of the transformants containing the plasmid. Thus, not every geneticin resistant colony is a true transformant. It has been reported that Ap$^R$ can be expressed in *S. cerevisiae* but the latter is resistant to ampicillin without the presence of Ap$^R$. Thus, Ap$^R$ cannot serve as a selection marker for yeast plasmid-mediated transformation. Nevertheless, yeasts that contain the highly expressed Ap$^R$ will produce sufficient penicillinase and make it possible to identify colonies containing such yeasts on special solid plates by the penicillinase test (Chevallier and Aigle, 1979). The latter test has provided a technique to identify the true transformants of *S. cerevisiae* and other yeasts from the geneticin resistant colonies.

Yeast xylose (or xylose and glucose) fermentation was carried out using the inventive recombinant yeasts under anaerobic conditions as described in Examples 6 through 9. The consumption of sugars (xylose and glucose) and the formation of ethanol and other products such as xylitol were followed during fermentation by taking samples and analyzing them by HPLC as further described in Example 6.

For example, pLNH21 (FIG. 5) was used to transform *S. cerevisiae*. The resulting transformant containing pLNH21 is designated SC(pLNH21), and can ferment 5% xylose nearly totally to ethanol in two to four days as demonstrated in FIG. 6A.

Figure 8A:
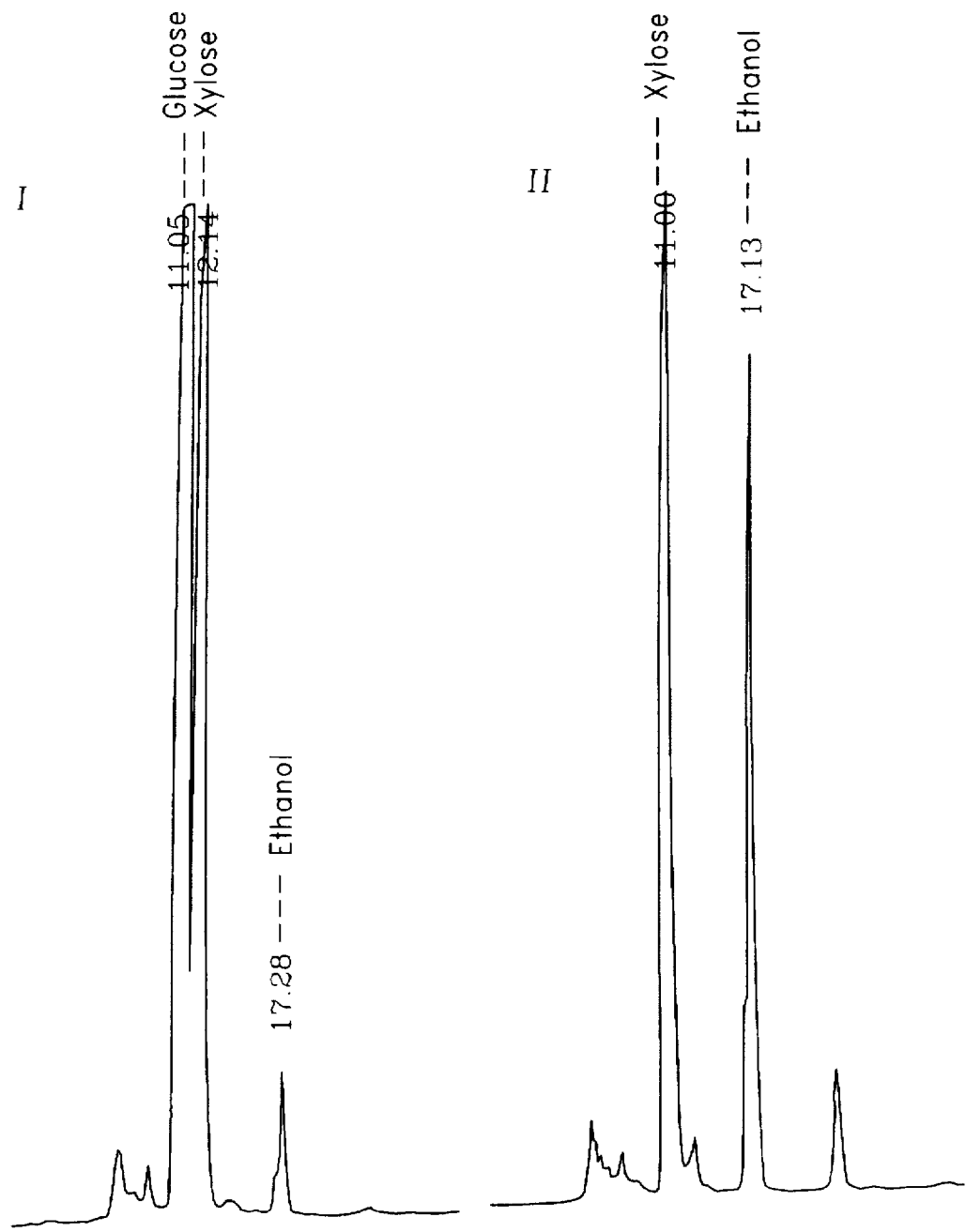
FIG. 8A shows an HPLC chromatogram of a fermentation broth obtained by fermenting a glucose- and xylose-containing medium (10% and 5%, respectively) with un-engineered yeast strain 1400 (containing no introduced XR, XD or XK genes) for (I) 0 days; and (II) 2 days, as further described in Example 8.
Figure 8B:
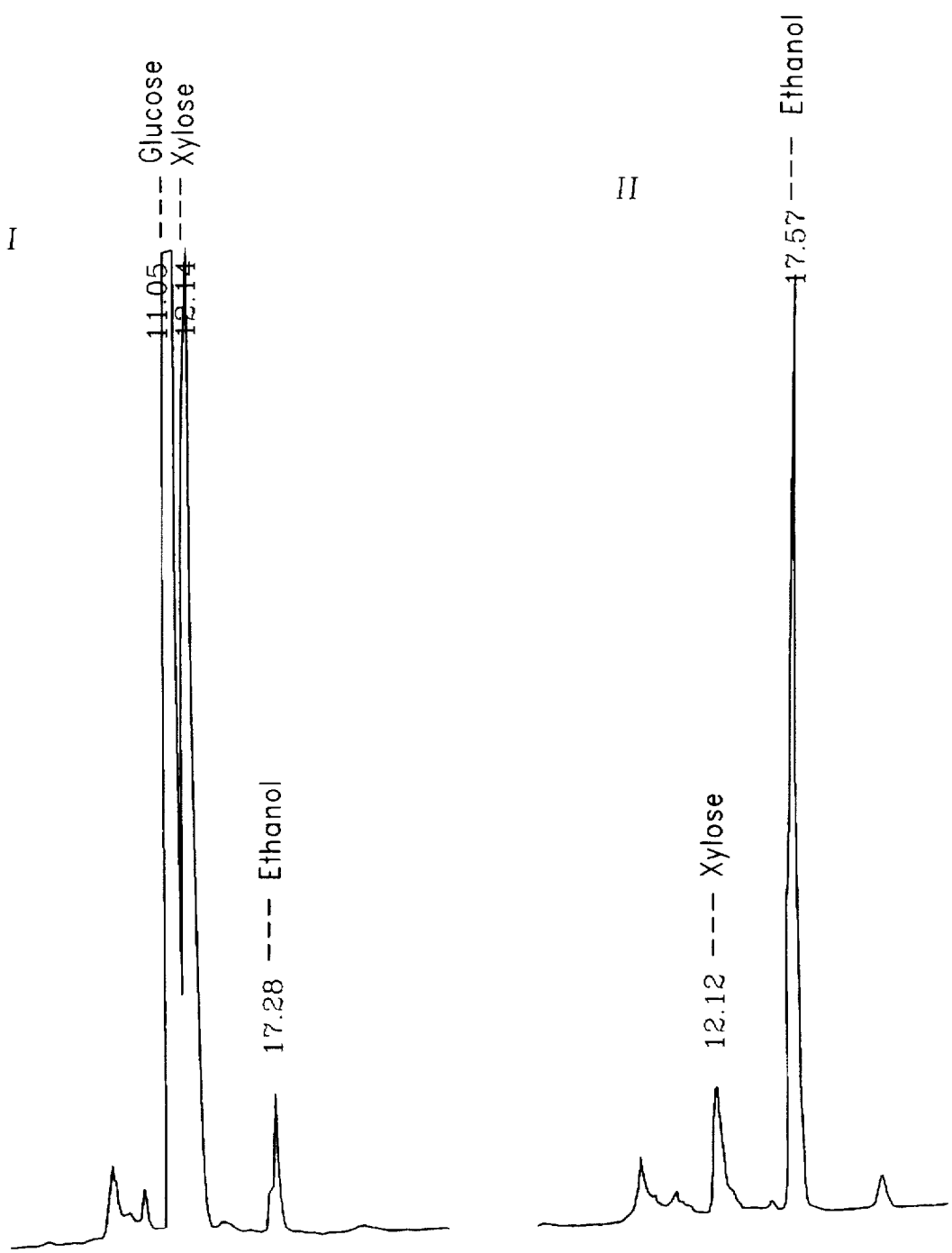
FIG. 8B shows an HPLC chromatogram of a fermentation broth obtained by fermenting a glucose- and xylose-containing medium (10% and 5%, respectively) with recombinant yeast 1400 (pLNH33) (yeast 1400 containing introduced XR, XD and XK genes) for (I) 0 days; and (II) 2 days, as further described in Example 8.

As an additional example, pLNH33 (FIG. 7) was used to transform yeast strain 1400 which is closely related to *S. cerevisiae* and has high tolerance to alcohol and temperature (D'Amore et al., 1989; D'Amore, 1990). The resultant genetically engineered yeast, designated 1400(pLNH33), can ferment 10% glucose and 5% xylose totally to ethanol in two to four days, without requiring high cell densities, as shown in FIGS. 8A and 8B.

pLNH33 is a more effective plasmid than pLNH21 for xylose fermentation because it is a higher copy-number plasmid. Furthermore, the XK in pLNH33 is fused to a more efficient promoter than the XK in pLNH21. *S. cerevisiae* has also been transformed with pLNH33, designated SC(pLNH33). Although SC(pLNH33) is much more effective in fermenting xylose or mixtures of xylose and glucose than SC(pLNH21), 1400(pLNH33) was found to be more effective in fermenting mixtures of glucose and xylose than SC(pLNH33). Thus, individual strains also affect the efficiency of fermentation. Similar to *S. cerevisiae*, the unengineered strain 1400 cannot use or ferment xylose (alone or in a mixture of glucose and xylose) as shown in FIG. 8B.

Generally, the results of these fermentive tests demonstrate that it is necessary that the yeast contain three introduced genes, XR, XD, and XK which have been properly fused to suitable promotors (preferably efficient glycolytic or other promoters that are not subject to glucose inhibition, and do not require xylose for induction) and to coordinately express these genes to make the yeast capable of fermenting xylose to ethanol only, and not to other by-products such as xylitol.

The results further demonstrate the importance of cloning a xylulokinase gene (XK) in addition to XR and XD in order to make yeasts ferment xylose effectively, particularly to ferment both glucose and xylose simultaneously when they are present in the same medium, such as in the hydrolyzates of cellulosic biomass. Similar to XR and XD, the cloned XK is preferably fused to a suitable efficient glycolytic or other promoter that is not subject to glucose inhibition, and which further does not require xylose for induction.

Figure 13:
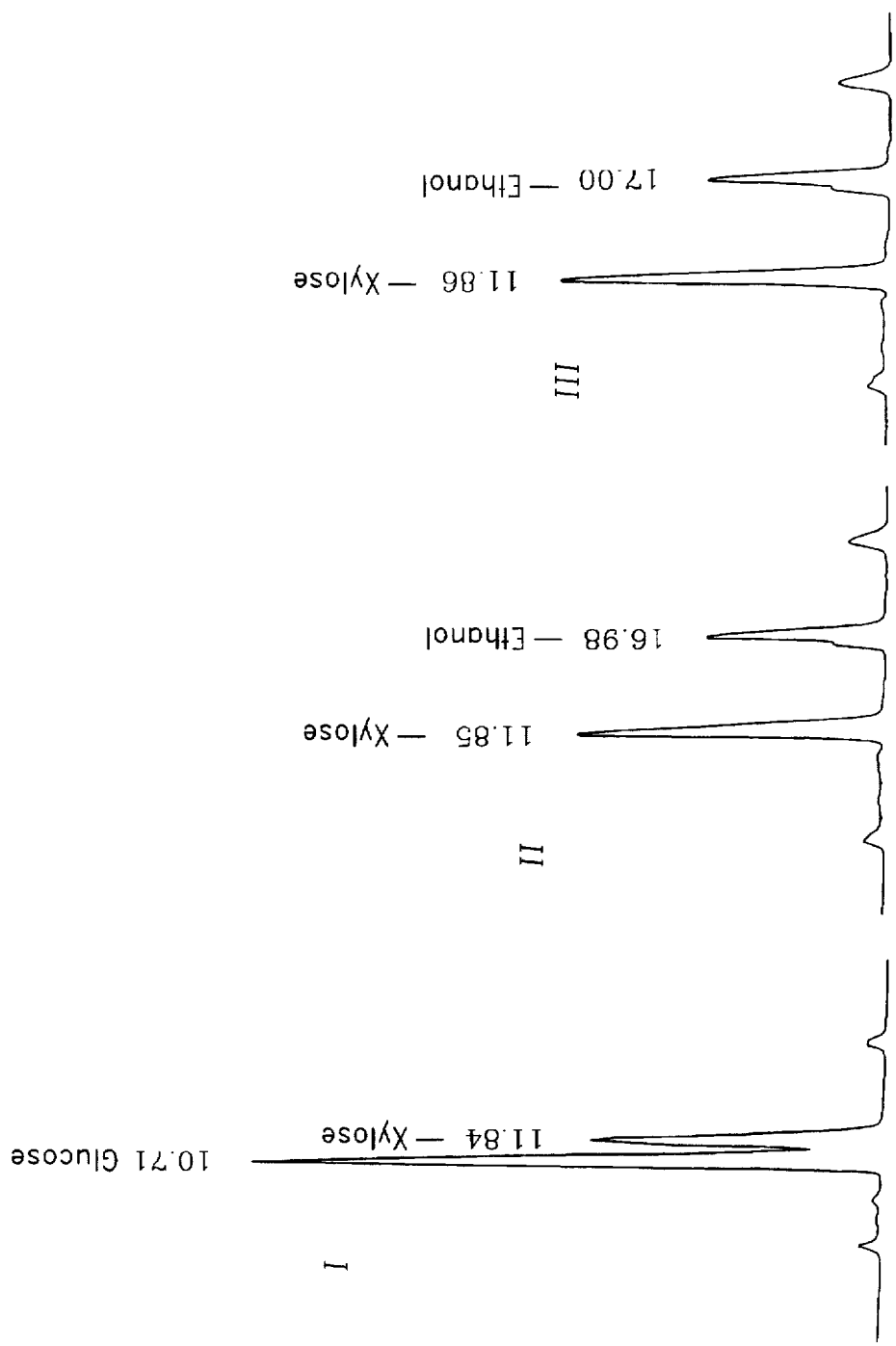
FIG. 13 shows an HPLC chromatogram of a fermentation broth obtained by fermenting a mixture of glucose (10%) and xylose (5%) with *S. cerevesiae* SC (pLNH13-32) (containing only the XR and XD genes) for (I) 0 days; (II) 2 days; and (III) 5 days.
Figure 14:
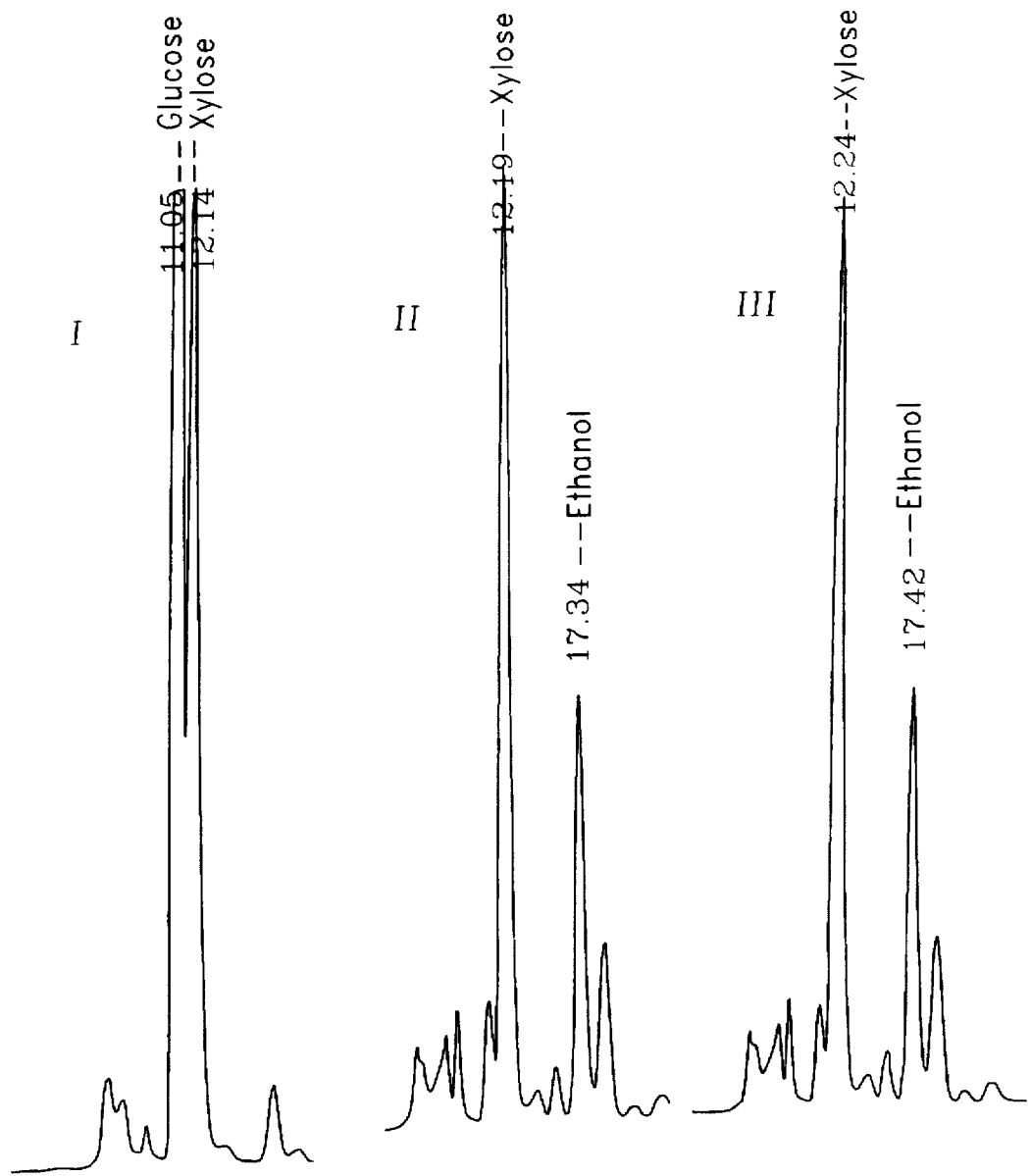
FIG. 14 shows an HPLC chromatogram of the fermentation broth obtained by fermenting a mixture of glucose (10%) and xylose (5%) with unengineered *Pichia stipitis* for (I) 0 days; (II) 3 days; and (III) 5 days.

Also, the applicants found that yeast containing just the cloned XR an XD can only ferment glucose but not xylose to ethanol when both these sugars are present in the culture medium together (see FIG. 13). Moreover, the applicants' results demonstrate that it is necessary for any yeast, including those xylose fermenting yeasts such as *P. stipitis* and *C. shihatae* to contain XR, XD and XK, fused to promoters that are not inhibited by the presence of glucose and also not requiring the use of xylose for induction in order to be able to ferment both glucose and xylose to ethanol when both these sugars are present together in the culture medium. FIG. 13 demonstrates that *S. cerevisiae* and related species containing only the cloned XR and XD genes, fused to proper promotors, can only ferment glucose but not xylose to ethanol when both these sugars are present in the culture medium. Similarly, FIG. 14 demonstrates that unengineered *P. stimitis* containing its original XR, XD, and XK can ferment xylose when the latter sugar is the sole carbon source of the medium (results not shown) but it cannot ferment xylose when both glucose and xylose are the carbon sources present in the same medium.

It will be understood that for those yeasts that contain low levels of xylulokinase activity, introducing the XK gene serves two purposes. One is to improve the level of the enzyme activity. High levels of XK activity are important for more advantageous yeast fermentation of xylose to ethanol as opposed to xylitol. The other is to place the gene under the control of an efficient promoter that will not be inhibited by the presence of glucose. It is well known that natural wild-type microorganisms including yeasts cannot use other sugars for growth and fermentation if glucose is present in the cultural medium. Glucose will inhibit the synthesis of the enzymes required for metabolizing other sugar molecules (the so called "glucose" effect). Thus promotors from genes for the synthesis of sugar molecule metabolizing enzymes excluding glucose will not be preferred since these will not provide simultaneous fermentation of the two abundant sugars. In addition, it was found in the applicants' work that cell growth is also a prerequisit for induction. Thus, promotors requiring xylose for induction are not preferred for the expression of XR, XD or XK.

For the purpose of promoting a further understanding of the present invention and its advantages, the following Examples are provided. It will be understood that these Examples are illustrative, and not limiting, in nature.

EXAMPLE 1

Synthesizing the XR and XD genes by PCR

The synthesis of the intact or promotorless XR by PCR has been previously described (Chen and Ho, 1993). For the synthesis of XD by PCR, three oligonucleotides according to the nucleotide sequence of XD (Köetter et al., 1990) were synthesized and are listed below:

Oligonucleotide I: pTCTAGACCACCCTAAGTCG (SEQ ID NO: 2)

Oligonucleotide II: pCACACAATTAAAATGA (Seq. I.D. No: 3)

Oligonucleotide III: pGGATCCACTATAGTCGAAG (Seq. I.D. No: 4)

Figure 10:
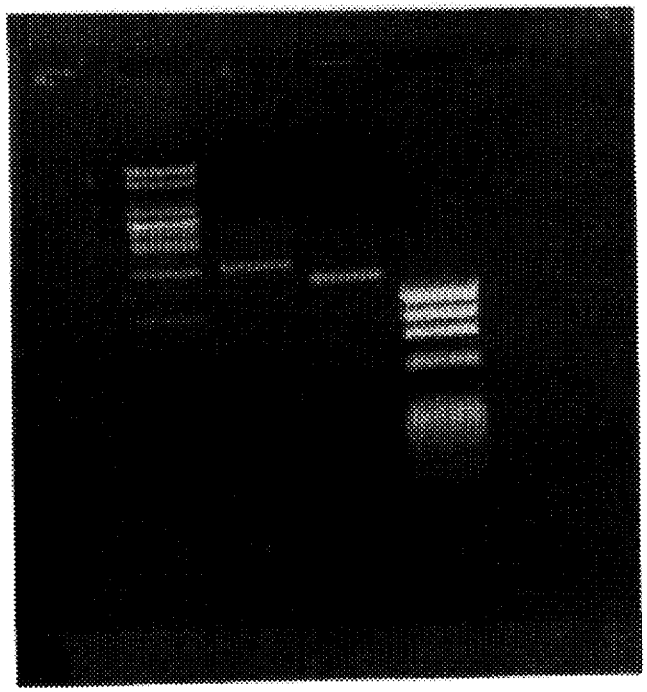
FIG. 10 shows direct amplification of the intact xylitol dehydrogenase gene and the promotorless XD from *P. stipitis* chromosomal DNA by the polymerase chain reaction (PCR) technique; from left, Lane 1: Molecular markers BamHI-EcoRI digested λ DNA; Lane 2: Pichia xylitol dehydrogenase gene (intact); Lane 3: Pichia xylitol dehydrogenase gene (promotorless); and Lane 4: Molecular markers, HaeIII digested φX DNA.

Oligonucleotides I and II were used to synthesize the intact XD gene and oligonucleotides II and III were used to synthesize the promotorless XD as shown in FIG. 10. The intact XD and the promotorless XD were first cloned in pKS(-) plasmid. The intact XR was then subcloned on pUCKm10 (FIG. 4) and the resulting plasmid pUCKm10-XD, was used to transform S. cerevisiae by electroporation as described in Example 5. The yeast transformants were used to assay the xylitol dehydrogenase activity to demonstrate that the cloned gene is intact and can be expressed in S. cerevisiae.

EXAMPLE 2

Fusion of the promotorless XD gene to the yeast pyruvate kinase gene promotor

Fusion of the XD gene to $P_{PK}$ was chosen to illustrate the precise fusion of xylose metabolizing genes to intact promotors by site-directed mutagenesis. These promotors are either glycolytic promotors or promotors that will not be inhibited by the presence of glucose in the culture medium and also will not require the presence of xylose for induction.

The promoter fragment of yeast pyruvate kinase from −910 to +23 (Burke et al., 1983) was synthesized by PCR as described in Example 1 for the synthesis of the XD gene. Both the $P_{PK}$ fragment and the promotorless XD were subcloned on pKS(-) plasmid and the undesired nucleotides between the $P_{PK}$ and the intact XD structural gene were removed by site-specific mutagenesis according to the procedure of Kunkel (Kunkel, 1987). The resulting fused gene contains −910 to −1 promoter fragments from the pyruvate kinase gene and +1 to +1963 nucleotides from the Pichia XD gene. The resulting pKS(-) plasmid containing $P_{PK}$-XD (or KD) is designated pKS(-)-KD or pKD2.

EXAMPLE 3

Analysis of the nucleotide sequence of yeast xylulokinase gene

Figure 11:
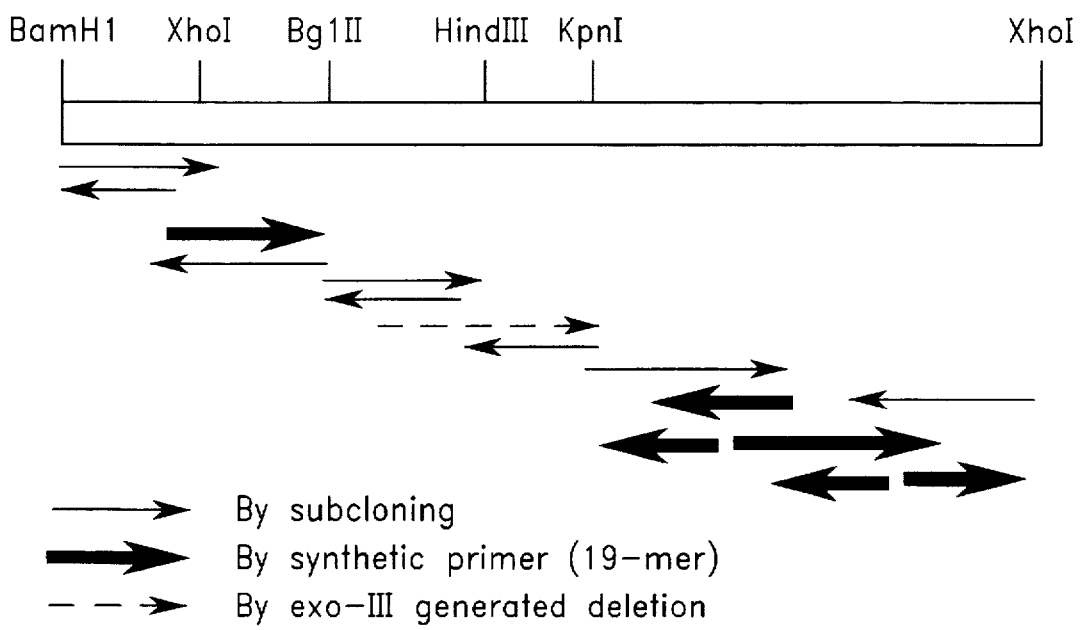
FIG. 11 diagrams the strategies used for sequencing the yeast xylulokinase gene.

The cloning of a 7.0 kb yeast (S. cerevisiae) DNA fragment that contains the yeast xylulokinase gene has been previously reported (Ho and Chang, 1989). By subcloning, the XK gene has been located on a 2.4 kb fragment. The nucleotide sequence of the 2.4 kb fragment has been analyzed. The 5' non-coding region contains 345 nucleotides, the translated region contains 2118 nucleotides, and the xylulokinase encoded by XK has 591 amino acids as shown in FIG. 2. The strategy used for sequencing the XK gene is shown in FIG. 11.

EXMPLE 4

Construction of intact ADCl promoter

Plasmid pMA56 (Ammerer, 1983) contains the yeast alcohol dehydrogenase I promoter ($P_{ADCl}$). The applicants have used this promoter to modify some of the genes in their work. For example, $P_{ADCl}$ has been fused to XR, and the resulting gene has been designated $P_{ADCl}$-XR or AR. Nevertheless, this $P_{ADCl}$ is not intact and does not contain the −1 to −14 nucleotides of the intact ADCl promoter (Bennetzen and Hall, 1982). The −1 to −14 region of a gene is usually very significant for controlling protein synthesis. Any gene fused to such a promoter has to rely on its original genetic signal for controlling the synthesis of its protein product.

In order to better control the expression of the gene fused to the ADCl promoter, the applicants employed site-specific mutagenesis to add the missing nucleotides (−1 to −14) to the ADCl promoter cloned on pMA56. The new intact ADCl promoter is designated P*$_{ADCl}$. This promoter has been used to modify XR and the resulting gene is designated as P*$_{ADCl}$-XR or A*R.

EXAMPLE 5

Construction of plasmid pLNH21 (also designated as pLSK15-KD-AR) and transformation of S. cerevisiae and 1400 with pLNH21

Figure 12:
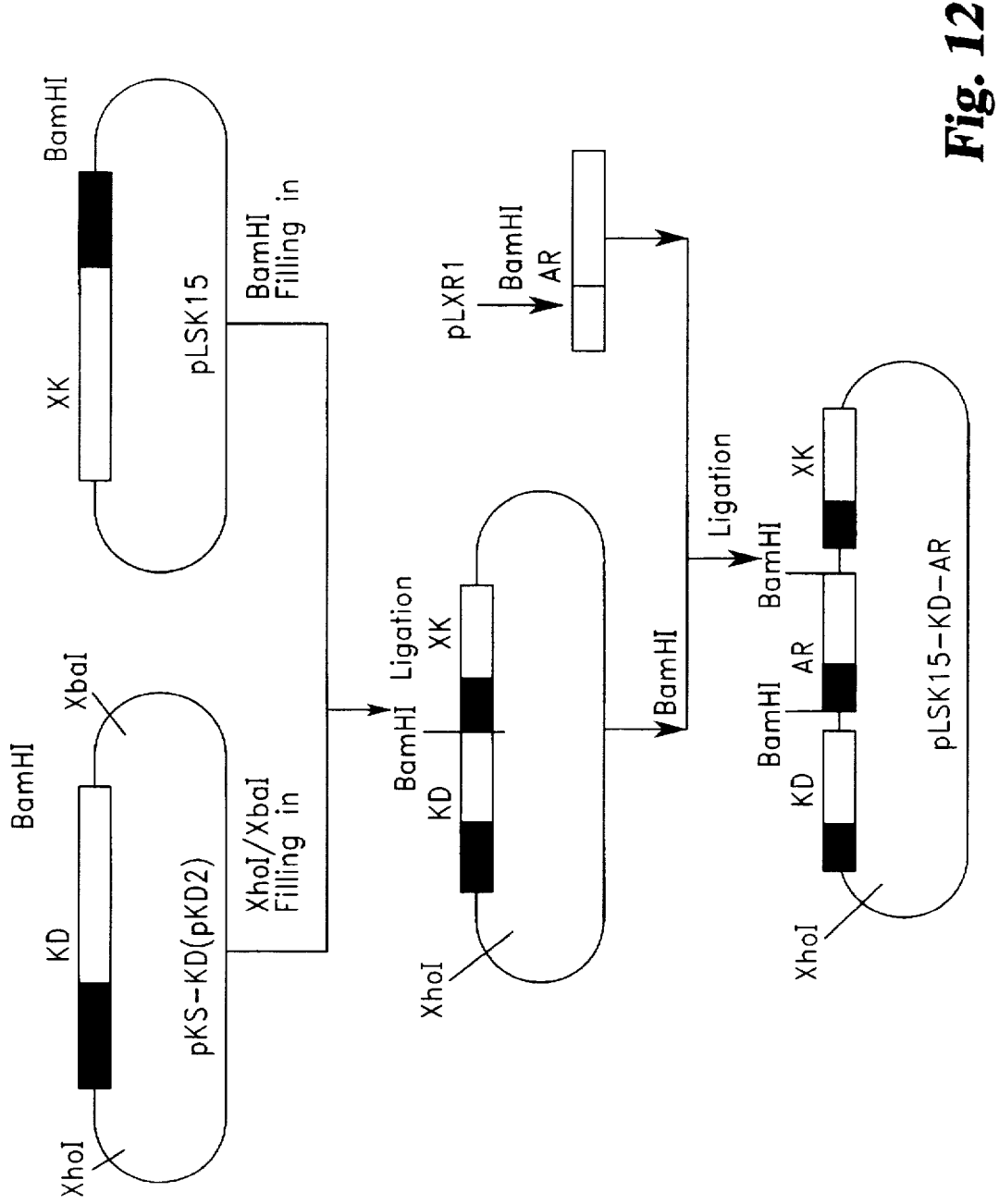
FIG. 12 is a schematic diagram outlining the construction of the plasmid pLNH21.

The construction of pLNH21 is outlined in FIG. 12. pLNH21 was used to transform S. cerevisiae and strain 1400 by electroporation under the following conditions. Fifty ml yeast cells, grown to early log phase (Klett Unit (KU) 130), were centrifuged to remove the medium, washed twice with cold water, once with cold 1M sorbitol, and resuspended in 200 µl 1M sorbitol. Sixty µl of the cells were transferred into a 4 ml presterilized plastic tube (with cap) and to which 0.1 µg to 1 µg plasmid DNA was added. Fifty µl of the resulting cells and plasmid mixture were pipetted into a precooled gene pulser cuvette with a 0.2 cm electrode gap and the content in the cuvette was subjected to pulse by the gene pulser with a pulse controller (BioRad) at 2.0 KV, 25 µF, 200 ohms.

Immediately, 0.50 ml YEPD (1% yeast extract, 2% peptone, and 2% glucose) was added to the cuvette. The content of the cuvette was transferred to a new 4 ml sterilized plastic tube and incubated at 30° C. for 1 hr. 100 µl of the cells were plated on agar plates containing YEPD and 50 µg/ml G418 (geneticin). Fast growing colonies were selected and replicated on another plate containing the same medium. The selected colonies were subjected to the ampicillin test (Chevallier and Aigle, 1979) until a positive one was identified. The above-described electroporation procedure is based on that reported by Becker and Guarente (1971). Our method for the selection of G418 resistant transformants is very effective and most of the selected colonies that were replicated on plates containing YEPD plus 50 µg/ml G418 were positive for the penicillinase test.

Transformation of strain 1400 with pLNH21 or other plasmids was carried out using a similar procedure to that described above, except that the cells were grown to 140–190 KU rather than 130 KU and the YEPD plates for the initial selection of transformants after electroporation contained 40 µg/ml geneticin G418 rather than 50. Transformation of strain 1400 by the above described procedures was not as effective as transformation of S. cerevisiae.

EXAMPLE 6

Fermentation of xylose with engineered SC (pLNH21), SC(pLNH13-32), and un-engineered parent S. cerevisiae These three yeasts were cultured in rich medium YEPD aerobically under identical conditions (SC(pLNH13-32) was constructed by transforming S. cerevisiae with a plasmid, designated pLNH13-32, which contains only the XR and XD gene/promotor combinations). These yeast cells were then used to ferment 5% xylose in YEP (1% yeast extract, 2% peptone) medium anaerobically also under identical conditions. The consumption of xylose and the formation of ethanol and xylitol were followed during fermentation by taking samples at proper intervals and analyzing them by HPLC under the following conditions.

The samples containing the fermentation broth (0.6 ml to 1.0 ml) removed from the cultures were kept in 1.5 ml Eppendorf tubes. The cells and other residues were first removed by centrifugation. The supernatant was further filtered by using sterile aerodisc (Gelman Sciences), 0.2 or 0.45 mm, syringe filters. The resulting filtrate from each sample was analyzed for its ethanol, glucose, xylose, and xylitol contents by high performance liquid chromatography (HPLC), using a Hitachi system according to the following conditions.

Column: Aminex HPX-87C, 300×7.8 mm
  Mobile phase: water
  Flow rate: 0.8 ml/min.
  Detection: Hitachi L-3350 RI detector
  Temperature: 80° C.
  Injection volume: 20 µl The results, shown in FIGS. 6A, 6B, and 6C (ethanol peaks in these and other Figures are actually 2½ times smaller than they should be due to the sensitivity of the instrument), demonstrate that only the engineered yeast SC(pLNH21) containing the cloned XR, XD, and XK can ferment high concentrations of xylose (5%) to ethanol, not the un-engineered parent S. cerevisiae, and also not the engineered SC(pLNH13-32) which only contains the cloned XD and XR, not XK. SC(pLNH13-32) ferments xylose mostly to xylitol.

EXAMPLE 8

Effective Fermentation of High Concentrations of both glucose and xylose by 1400(pLNH33) to ethanol A mixture of glucose and xylose (approximately 10% glucose and 5% xylose) were fermented by strain 1400 and 1400(pLNH33) under identical conditions. These yeasts were kept on agar plates containing the proper media and were inoculated directly from the agar plates into 50 ml of YEPD medium (1% Yeast extract, 2% peptone, and 2% glucose) in a 250 ml Erlenmeyer flask equipped with a side-arm which allows direct monitoring of the growth of the yeast cultures by the Klett colorimeter. The cultures were incubated in a shaker at 30° C. and 200 rpm aerobically.

When the cell density reached mid-log phase (400 Klett units), 12.5 ml (40%) glucose and 6.25 ml (40%) xylose were added to each flask. After thorough mixing, 1 ml of the culture mixture was removed from the flask to serve as the zero sample. The flask was then sealed with Saran wrap to allow fermentation to be carried out anaerobically. One ml samples of the fermentation broth (with some cells) were removed at proper intervals (every 24 hr.) to serve as samples for measuring the sugar and ethanol contents of the broth during fermentation. The ethanol, glucose, xylose, and xylitol contents of the samples were analyzed by HPLC as described in Example 6. The results, shown in FIGS. 8A and 8B, demonstrate that the genetically engineered yeast 1400 (pLNH33) can ferment 10% glucose and 5% xylose to ethanol simultaneously in two to four days without requiring high cell density. On the other hand, the parent strain 1400 can only convert glucose to ethanol but not xylose. The fermentation was carried out under normal conditions, without requiring special medium, special pH, and also without requiring growth of yeast to high cell density. Thus the genetically engineered 1400(pLNH33) containing the XR, XD, and XK, all fused to glycolytic promotors and cloned on a high copy-number plasmid pUCKm10, can ferment high concentrations of both glucose and xylose simultaneously to ethanol in two to four days with very little xylitol produced as a by-product.

EXAMPLE 9

Attempted Fermentation of xylose/glucose with engineered SC(pLNH13-32)

The fermentation procedure of Example 8 was repeated except using S. cerevisiae SC (pLNH13-32) (containing only the XR and XD genes) as the fermentive organism. The results, shown in FIG. 13, demonstrate that such a genetic unengineered yeast containing only the XR and XD genes can ferment glucose but not xylose when both of these sugars are present in the fermented medium.

EXAMPLE 10

Attempted Fermentation of xylose/glucose with unengineered Pichia stipitis

The fermentation procedure of Example 8 was repeated, except using unengineered Pichia stipitis as the fermentive organsim. Samples of the fermentation broth were analyzed by HPLC after fermentation for (I) 0 day; (II) 3 days; and (III) 5 days. The results, shown in FIG. 14, demonstrate that P. stipitis can only ferment glucose, but not xylose when both of these sugars are present in the same medium.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

REFERENCES

The following references, to the extent that they provide exemplary procedural or other details supplementary to those set forth herein, are specifically incorporated herein by reference.

Ammerer, G., "Expression of genes in yeast using the ADC1 promoter," Methods in Enzymol. 101, 192–201 (1983).

Amore, R., M. Wilhelm, and C. P. Hollenberg, "The fermentation of xylose: An analysis of the expression of Bacillus and Actinoplanes xylose isomerase genes in yeast," Appl. Microbiol. Biotechnol., 30(4), 351–357 (1989).

Becker, D., and L. Guarente, "High efficiency transformation of yeast by electroporation," Methods in Enzymol. 194, 182–186 (1991).

Bennetzen, J. L. and B. D. Hall, "The primary structure of the Saccharomyces cerevisiae gene for alcohol dehydrogenase I," J. Biol. Chem., 257(6), 3018–3025 (1982).

Burke, R. L.,P. Tekamp-Olson, and R. Najarian, "The isolation, characterization, and sequence of the pyruvate kinase gene of Saccharomyces cerevisiae," J. Biol. Chem. 258(4) 2193–2201 (1983).

Chang, S. F. and N. W. Y. Ho, "Cloning the yeast xylulokinase gene for the improvement of xylose fermentation." Appl. Biochem Biotechnol. 17, 313–318 (1988).

Chen, Zhengdao, and N. W. Y. Ho, "Cloning and improving the expression of Pichia stipitis xylose reductase gene in Saccharomyces cerevisiae," Appl. Biochem. Biotechnol., 39–40, 135–147 (1993).

Chevallier, M. R. and M. Aigle, "Qualitative detection of penicillinase produced by yeast strains carrying chimeric yeast-coli plasmids," FEBS Letters, 108(1) 179–184 (1979).

Chiang, L-C, H-Y. Hsiao, P. P. Ueng, L-F. Chem, and G. T. Tsao. "Ethanol production from xylose by enzymic isomerization and yeast fermentation," Biotechnol. Bioeng., 11, 263–274 (1981).

D'Amore, C. G., I. Russell, and G. G. Stewart. "Selection and optimization of yeast suitable for ethanol production at 400° C.," Enz. Microbiol. Technol., 11, 411 (1989). D'Amore, T., C. J. Panchal, I. Russell, and G. G. Stewart, "A study of ethanol tolerance in yeast: Critical Reviews," Biotechnol., 9, 287 (1990).

Deng, X. X. and N. W. Y. Ho, "Xylulokinase activity in various yeasts including Sacharomyces cerevisiae containing the cloned xylulokinase gene," Appl. Biochem. Biotechnol., 24–25, 193 (1990).

DuPreez, J. C. and J. P. van der Walt, "Fermentation of D-xylose to ethanol by a strain by Candida shehatae," Biotechnol. Lett., 5, 357–362 (1983).

Grootjen, D. R. J., R. G. J. M. van der lans, and K. Ch. A. M. Luyben, "Effects of the aeration rate on the fermentation of glucose and xylose by Pichia stipitis CBS 5773, Enzyme Microb. Technol., 12, 20–23 (1990).

Hallborn, J., M. Walfridsson, U. Airaksinen, H. Ojamo, B. Hahn-Hagerdal, M. Penttila, and S. Keranen, "Xylitol production by recombinant Saccharomyces cerevisiae, Bio./ Technol., 9, 1090 (1991).

Ho, N. W. Y., and S-F. Chang, "Cloning of yeast xylulokinase gene by complementation of E. coli and yeast mutations," Enzyme Microb. Technol., 11, 417 (1989).

Ho, N. W. Y., P. Stevis, S. Rosenfeld, J. J. Huang, and G. T. Tsao, "Expression of E. coli xylose isomerase gene by a yeast promoter," Biotechnology and Bioenginering Symposium, No. 13, 245–250 (1983).

Holland, J. P. and M. J. Holland, "The primary structure of a glyceraldehyde-3-phosphate dehydrogenase gene from Saccharomyces cerevisiae," J. Biol. Chem. 253(19) 9839–9845 (1979).

Jeffries, T. W., "Emerging technology for fermenting D-xylose: Trends in biotechnology 3(8), 208–212 (1985).

Jeffries, T. W., "Utilization of xylose by bacteria, yeasts, and fungi," Adv. in Biochem. Engr. Biotechnol. 27, 1–32 (1983).

Köetter, P., R. Amore, C. P. Hollenberg, and M. Ciriacy, "Isolation and characterization of the Pichia stipitis xylitol dehydrogenase gene, XYL2, and construction of a xylose-utilizing Saccharomyces cerevisiae transformant," Curr. Genet., 18, 493–500 (1990).

Kötter, P. and M. Ciriacy, "Xylose fermentation by Saccharomyces cerevisiae," Appl. Microbiol. Biotechnol., 38, 776–783 (1993).

Kunkel, T. A., J. P. Roberts, and R. a. Zakour, "Rapid and efficient site-specific mutagenesis without phenotypic selection," Methods Enzymol., 154, 367–382 (1987).

Lastick, S., M. Y. Tucker, J. R. Beyett, G. R. Noll, and K. Grohmann. "Simultaneous fermentation and isomerization of xylose to ethanol," Appl. Microbiol. Biotechnol., 30, 574–579 (1989).

Rosenfeld, S., P. Stevis, and N. W. Y. Ho, "Cloning and characterization of the xyl genes from E. coli," Mol. Gen. Genetics, 194, 410–415 (1984).

Sarthy, A. V., et al., "Expression of the E. coli xylose isomerase gene in S. cerevisiae, Appl. Environ. Microb., 53, 1996–2000 (1987).

Stevis, P. A., J. J. Huang, N. W. Y. Ho, "Cloning of the pachysolen tannophilus xylulokinase gene by complementation in Escherichia coli." Appl Environ. Micro.(53) 1, 2975–2977 (1987).

Stevis, P. A. and N. W. Y. Ho, "Overproduction of D-xylose isomerase in E. coli by Cloning the D-xylose Isomerase gene", Enzyme Microb. Technol. Vol. 7, pp. 592–596 (1985).

Strasser, A. W. M., C. P. Hollenberg, M. Ciriacy, P. K öetter, R. Amore, M. Piontek, and J. Hagedorn, "Cloning of yeast xylose reductase and xylitol dehydrogenase genes and their use," German patent application (1990).

Takuma, S., N. Nakashima, M. Tantirungkij, S. Kinoshita, H. Okada, T. Seki, and T. Yoshida, "Isolation of xylose reductase gene of Pichia stipitis and its expression in Saccharomyces cerevisiae," Appl. Biochem. Biotechnol., 27–28, 327 (1991).

Toivola, A., D. Yarrow, E. van den Bosch, J. P. van Dijken, and W. A. Scheffers. "Alcoholic fermentation of D-xylose by yeasts," Appl. Environ. Microbiol., 47(6), 1221–1223 (1984).

Wilhelm, M., and C. P. Hollenberg, "Selective cloning of Bacillus subtilis xylose isomerase and xylulokinase in E. coli genes by IS5-mediated expression," the EMBO Journal, 3, 2555–2560 (1984).

Zalkin, H. and C. Yanofsky, J. Biol. Chem. 257, 1491–1500 (1982).

What is claimed is:

1. A recombinant yeast containing introduced genes encoding xylose reductase, xylitol dehydrogenase and xylulokinase and which ferments xylose to ethanol.

2. The recombinant yeast of claim 1 wherein the yeast also ferments glucose to ethanol.

3. The recombinant yeast of claim 2 wherein the yeast is of the genus Saccharomyces.

4. The recombinant yeast of claim 3 wherein said genes are fused to non-glucose-inhibited promoters and the yeast simultaneously ferments glucose and xylose to ethanol.

5. A recombinant DNA molecule comprising genes encoding xylose reductase, xylitol dehydrogenase and xylulokinase.

6. The recombinant DNA molecule of claim 5 wherein said genes are fused to non-glucose-inhibited promoters.

7. A vector effective for transforming yeast and comprising genes encoding xylose reductase, xylitol dehydrogenase and xylulokinase.

8. The vector of claim 7 wherein said genes are fused to non-glucose-inhibited promoters.

9. A method for obtaining a recombinant yeast which ferments xylose to ethanol, comprising introducing DNA into a yeast so as to cause the yeast to have introduced genes encoding xylose reductase, xylitol dehydrogenase and xylulokinase.

10. The method of claim 9 wherein said introduced DNA comprises genes encoding xylose reductase, xylitol dehydrogenase and xylulokinase.

11. The method of claim 9 wherein said yeast is of the genus Saccharomyces.

12. The method of claim 10 wherein the medium also contains glucose and the yeast also ferments said glucose to ethanol.

13. A method for fermenting xylose to ethanol, comprising fermenting a xylose-containing medium with a recombinant yeast containing introduced genes encoding xylose reductase, xylitol dehydrogenase and xylulokinase and which ferments xylose to ethanol.

14. The method of claim 2 wherein the yeast is of the genus Saccharomyces.

15. The method of claim 14 wherein said genes are fused to non-glucose-inhibited promoters and the yeast simultaneously ferments glucose and xylose to ethanol.

16. A method for fermenting glucose to ethanol, comprising fermenting a glucose-containing medium with a recombinant yeast containing introduced genes encoding xylose reductase, xylitol dehydrogenase and xylulokinase and which ferments xylose and glucose to ethanol.

17. The method of claim 16 wherein said medium also contains xylose.

18. The method of claim 17 wherein said yeast is of the genus Saccharomyces.

19. A recombinant yeast containing genes encoding xylose reductase, xylitol dehydrogenase and xylulokinase, wherein said genes are fused to non-glucose-inhibited promoters and wherein said yeast ferments xylose to ethanol.

20. The recombinant yeast of claim 19 wherein said yeast also ferments glucose to ethanol.

* * * * *

UNITED STATES PATENT AND TRADEMARK OFFICE
CERTIFICATE OF CORRECTION

PATENT NO. : 5,789,210
DATED : August 4, 1998
INVENTOR(S) : Nancy W.Y. Ho et al.

It is certified that error appears in the above-indentified patent and that said Letters Patent is hereby corrected as shown below:

In col. 5, line 31, please delete "$ANK^+$" and insert in lieu thereof --$NAD^+$--.

In col. 6, line 19, please delete "FIG. 2" and insert in lieu thereof --Figures 2a and 2b--.

In col. 8, line 63, please delete "stimitis" and insert in lieu thereof --stipitis--.

In col. 10, line 22, please delete "FIG. 2" and insert in lieu thereof --Figures 2a and 2b--.

In col. 10, line 25, please delete "EXMPLE" and insert in lieu thereof --EXAMPLE--.

In col. 12, line 8, please delete "(pLNI133)" and insert in lieu thereof --(pLNH33)--.

In col. 13, line 47, please delete "400° C." and insert in lieu thereof --40° C--.

In col. 13, line 52, please delete "Sacharomyces" and insert in lieu thereof --Saccharomyces--.

In col. 22, line 32, please delete "claim 2" and insert in lieu thereof --claim 13--.

Signed and Sealed this

Twenty-first Day of September, 1999

Q. TODD DICKINSON

*Attest:*

*Attesting Officer*          *Acting Commissioner of Patents and Trademarks*